(12) United States Patent
Quake et al.

(10) Patent No.: US 10,117,911 B2
(45) Date of Patent: Nov. 6, 2018

(54) COMPOSITIONS AND METHODS TO TREAT HERPES SIMPLEX VIRUS INFECTIONS

(71) Applicant: Agenovir Corporation, South San Francisco, CA (US)

(72) Inventors: Stephen R. Quake, Stanford, CA (US); Jianbin Wang, South San Francisco, CA (US)

(73) Assignee: Agenovir Corporation, South San Francisco, CA (US)

(*) Notice: Subject to any disclaimer, the term of this patent is extended or adjusted under 35 U.S.C. 154(b) by 0 days.

(21) Appl. No.: 15/167,204

(22) Filed: May 27, 2016

(65) Prior Publication Data

US 2016/0346361 A1 Dec. 1, 2016

Related U.S. Application Data

(60) Provisional application No. 62/168,259, filed on May 29, 2015.

(51) Int. Cl.
| | |
|---|---|
| *A61K 38/46* | (2006.01) |
| *C12N 9/16* | (2006.01) |
| *A61K 9/00* | (2006.01) |
| *A61K 9/08* | (2006.01) |
| *C12N 9/22* | (2006.01) |
| *C12N 7/00* | (2006.01) |
| *C12N 15/09* | (2006.01) |
| *C12N 15/52* | (2006.01) |
| *C12N 15/67* | (2006.01) |
| *A61K 39/12* | (2006.01) |
| *A61K 48/00* | (2006.01) |
| *A61K 38/00* | (2006.01) |
| *A61K 39/00* | (2006.01) |
| *A61K 31/04* | (2006.01) |
| *C07K 14/005* | (2006.01) |
| *C07K 14/195* | (2006.01) |

(52) U.S. Cl.
CPC .......... *A61K 38/465* (2013.01); *A61K 9/0014* (2013.01); *A61K 9/08* (2013.01); *C12N 9/16* (2013.01); *C12Y 301/00* (2013.01)

(58) Field of Classification Search
CPC . C12N 9/22; C12N 7/00; C12N 15/09; C12N 15/52; C12N 15/67; A61K 39/12; A61K 48/00; A61K 48/0066; A61K 38/00; A61K 2300/00; A61K 2039/525; A61K 39/40; A61P 31/04; A61P 31/12; C07K 14/005; C07K 14/195
See application file for complete search history.

(56) References Cited

U.S. PATENT DOCUMENTS

| | | | |
|---|---|---|---|
| 4,897,355 A | 1/1990 | Eppstein et al. | |
| 4,946,787 A | 8/1990 | Eppstein et al. | |
| 5,049,386 A | 9/1991 | Eppstein et al. | |
| 5,208,036 A | 5/1993 | Eppstein et al. | |
| 5,356,802 A | 10/1994 | Chandrasegaran | |
| 5,436,150 A | 7/1995 | Chandrasegaran | |
| 5,466,468 A | 11/1995 | Schneider et al. | |
| 5,487,994 A | 1/1996 | Chandrasegaran | |
| 5,580,571 A | 12/1996 | Hostetler | |
| 5,626,869 A | 5/1997 | Nyqvist et al. | |
| 5,789,538 A | 8/1998 | Rebar et al. | |
| 5,925,523 A | 7/1999 | Dove et al. | |
| 6,007,988 A | 12/1999 | Choo et al. | |
| 6,013,453 A | 1/2000 | Choo et al. | |
| 6,140,466 A | 10/2000 | Barbas, III et al. | |
| 6,200,759 B1 | 3/2001 | Dove et al. | |
| 6,242,568 B1 | 6/2001 | Barbas, III et al. | |
| 6,326,198 B1 | 12/2001 | Emerson et al. | |
| 6,335,195 B1 | 1/2002 | Rodgers et al. | |
| 6,338,942 B2 | 1/2002 | Kraus et al. | |
| 6,383,481 B1 | 5/2002 | Ikehara et al. | |
| 6,387,383 B1 | 5/2002 | Dow et al. | |
| 6,410,248 B1 | 6/2002 | Greisman et al. | |
| 6,453,242 B1 | 9/2002 | Eisenberg et al. | |
| 6,468,989 B1 | 10/2002 | Chang et al. | |
| 6,517,847 B2 | 2/2003 | Dow et al. | |
| 6,534,261 B1 | 3/2003 | Cox, III et al. | |
| 6,607,882 B1 | 8/2003 | Cox, III et al. | |
| 6,890,554 B2 | 5/2005 | Jessee et al. | |
| 7,166,298 B2 | 1/2007 | Jessee et al. | |
| 8,697,359 B1 | 4/2014 | Zhang | |

(Continued)

FOREIGN PATENT DOCUMENTS

| | | | |
|---|---|---|---|
| WO | 91/16024 A1 | 10/1991 | |
| WO | 91/17424 A1 | 11/1991 | |

(Continued)

OTHER PUBLICATIONS

Hay J, Ruyechan WT. "Chapter 10: Alphaherpesvirus DNA replication." Arvin A, Campadelli-Fiume G, Mocarski E, et al., editors. Human Herpesviruses: Biology, Therapy, and Immunoprophylaxis. Cambridge: Cambridge University Press; 2007.*

Masaoka T, Zhao H, Hirsch DR, D'Erasmo MP, Meck C, Varnado B, Gupta A, Meyers MJ, Baines J, Beutler JA, Murelli RP, Tang L, Le Grice SF. Characterization of the C-Terminal Nuclease Domain of Herpes Simplex Virus pUL15 as a Target of Nucleotidyltransferase Inhibitors. Biochemistry. Feb. 9, 2016;55(5):809-19. Epub Feb. 1, 2016.*

Selvarajan Sigamani S, Zhao H, Kamau YN, Baines JD, Tang L. The structure of the herpes simplex virus DNA-packaging terminase pUL15 nuclease domain suggests an evolutionary lineage among eukaryotic and prokaryotic viruses. J Virol. Jun. 2013;87(12):7140-8. Epub Apr. 17, 2013.*

(Continued)

*Primary Examiner* — Rachel B Gill
(74) *Attorney, Agent, or Firm* — Seed IP Law Group LLP

(57) ABSTRACT

Herpes simplex virus (HSV) including herpes simplex virus 1 and 2 (HSV-1 and HSV-2) are a persistent cause of human disease with no known cure. Guided nuclease systems target specific regions of the HSV-1 and HSV-2 genomes, disrupting the virus' nucleic acid and rendering even latent viruses incapacitated.

21 Claims, 26 Drawing Sheets

(56) References Cited

U.S. PATENT DOCUMENTS

| | | | |
|---|---|---|---|
| 8,865,406 B2 | 10/2014 | Zhang et al. | |
| 8,889,418 B2 | 11/2014 | Zhang et al. | |
| 8,906,616 B2 | 12/2014 | Zhang et al. | |
| 8,937,157 B2 | 1/2015 | Ledbetter et al. | |
| 8,945,839 B2 | 2/2015 | Zhang | |
| 8,993,233 B2 | 3/2015 | Zhang et al. | |
| 9,322,037 B2 | 4/2016 | Liu et al. | |
| 9,487,802 B2 | 11/2016 | Quake et al. | |
| 2004/0203124 A1 | 10/2004 | King et al. | |
| 2004/0265325 A1 | 12/2004 | Diamond et al. | |
| 2005/0064474 A1 | 3/2005 | Urnov et al. | |
| 2005/0222075 A1 | 10/2005 | Herweijer et al. | |
| 2006/0106321 A1 | 5/2006 | Lewinsky et al. | |
| 2006/0188987 A1 | 8/2006 | Guschin et al. | |
| 2008/0131962 A1 | 6/2008 | Miller | |
| 2009/0017543 A1 | 1/2009 | Wilkes et al. | |
| 2009/0047272 A1 | 2/2009 | Appelbaum et al. | |
| 2010/0076057 A1 | 3/2010 | Sontheimer et al. | |
| 2011/0023144 A1 | 1/2011 | Weinstein et al. | |
| 2011/0177594 A1 | 7/2011 | Shushan et al. | |
| 2012/0122213 A1 | 5/2012 | Lai et al. | |
| 2013/0046230 A1 | 2/2013 | Lewis, Jr. et al. | |
| 2013/0136768 A1 | 5/2013 | Picker et al. | |
| 2013/0149286 A1 | 6/2013 | Chretien et al. | |
| 2013/0165769 A1 | 6/2013 | Gerrans et al. | |
| 2013/0330778 A1 | 12/2013 | Zeiner et al. | |
| 2014/0017212 A1 | 1/2014 | Rebar | |
| 2014/0068797 A1 | 3/2014 | Doudna et al. | |
| 2014/0186843 A1 | 7/2014 | Zhang et al. | |
| 2014/0186958 A1 | 7/2014 | Zhang et al. | |
| 2014/0273037 A1 | 9/2014 | Wu | |
| 2014/0273233 A1 | 9/2014 | Chen et al. | |
| 2014/0295556 A1 | 10/2014 | Joung et al. | |
| 2014/0315985 A1 | 10/2014 | May et al. | |
| 2014/0342457 A1 | 11/2014 | Mali et al. | |
| 2014/0342458 A1 | 11/2014 | Mali et al. | |
| 2014/0349400 A1 | 11/2014 | Jakimo et al. | |
| 2014/0356958 A1 | 12/2014 | Mali et al. | |
| 2014/0357523 A1 | 12/2014 | Zeiner et al. | |
| 2015/0020223 A1 | 1/2015 | Zhang et al. | |
| 2015/0024500 A1 | 1/2015 | Yu et al. | |
| 2015/0045546 A1 | 2/2015 | Siksnys et al. | |
| 2015/0050699 A1 | 2/2015 | Siksnys et al. | |
| 2015/0056705 A1 | 2/2015 | Conway et al. | |
| 2015/0071898 A1 | 3/2015 | Liu et al. | |
| 2015/0071903 A1 | 3/2015 | Liu et al. | |
| 2015/0098954 A1 | 4/2015 | Hyde et al. | |
| 2015/0176006 A1 | 6/2015 | Krause et al. | |
| 2015/0232881 A1 | 8/2015 | Glucksmann et al. | |
| 2015/0232883 A1 | 8/2015 | Dahlman et al. | |
| 2015/0353905 A1 | 12/2015 | Weiss et al. | |
| 2015/0368670 A1 | 12/2015 | Quake et al. | |
| 2015/0376583 A1 | 12/2015 | Quake et al. | |
| 2016/0017301 A1 | 1/2016 | Khalili et al. | |
| 2016/0040165 A1 | 2/2016 | Howell et al. | |
| 2016/0060655 A1 | 3/2016 | Quake et al. | |
| 2016/0287678 A1 | 10/2016 | Wang | |
| 2016/0317677 A1 | 11/2016 | Bhatia et al. | |
| 2016/0346360 A1 | 12/2016 | Quake et al. | |
| 2016/0346361 A1 | 12/2016 | Quake et al. | |
| 2016/0346362 A1 | 12/2016 | Quake et al. | |
| 2016/0348074 A1 | 12/2016 | Quake et al. | |
| 2016/0350476 A1 | 12/2016 | Quake et al. | |
| 2017/0020994 A1* | 1/2017 | Bloom | A61K 31/522 |
| 2017/0049909 A1* | 2/2017 | Cullen | C12N 15/111 |

FOREIGN PATENT DOCUMENTS

| | | | | |
|---|---|---|---|---|
| WO | 2007/071994 A2 | 6/2007 | | |
| WO | 2010/056728 | 5/2010 | | |
| WO | 2013/029919 A1 | 3/2013 | | |
| WO | 2013/141680 A1 | 9/2013 | | |
| WO | 2013/142578 A1 | 9/2013 | | |
| WO | 2013/176772 A1 | 11/2013 | | |
| WO | 2013/188037 A2 | 12/2013 | | |
| WO | 2014/071235 A1 | 5/2014 | | |
| WO | 2014/093479 A1 | 6/2014 | | |
| WO | 2014/099744 A1 | 6/2014 | | |
| WO | 2014/124226 A1 | 8/2014 | | |
| WO | 2014/143381 A1 | 9/2014 | | |
| WO | 2014/150624 A1 | 9/2014 | | |
| WO | 2014/165349 A1 | 10/2014 | | |
| WO | 2014/172470 A2 | 10/2014 | | |
| WO | 2014204726 A1 | 12/2014 | | |
| WO | 2015/006290 A1 | 1/2015 | | |
| WO | 2015/006747 A2 | 1/2015 | | |
| WO | 2015/031775 A1 | 3/2015 | | |
| WO | 2015/034872 A2 | 3/2015 | | |
| WO | WO-2015031775 A1 * | 3/2015 | | A61K 48/00 |
| WO | 2015053995 A1 | 4/2015 | | |
| WO | 2015/066557 A1 | 5/2015 | | |
| WO | 2015/089465 A1 | 6/2015 | | |
| WO | WO 2015089465 A1 * | 6/2015 | | C12N 9/22 |
| WO | 2015/105928 A1 | 7/2015 | | |
| WO | 2015/126927 A2 | 8/2015 | | |
| WO | 2015/153889 A2 | 10/2015 | | |
| WO | 2015/184259 A1 | 12/2015 | | |
| WO | 2016/115355 A1 | 7/2016 | | |
| WO | 2016/197132 A1 | 12/2016 | | |
| WO | 2016/198500 A1 | 12/2016 | | |

OTHER PUBLICATIONS

Weller SK, Kuchta RD. The DNA helicase-primase complex as a target for herpes viral infection. Expert Opin Ther Targets. Oct. 2013;17(10):1119-32. Epub Aug. 12, 2013.*

Bi Y, Sun L, Gao D, Ding C, Li Z, Li Y, Cun W, Li Q. High-efficiency targeted editing of large viral genomes by RNA-guided nucleases. PLoS Pathog. May 1, 2014;10(5):e1004090. doi: 10.1371/journal.ppat.1004090. eCollection May 2014.*

Bazhulina NP, Surovaya AN, Gursky YG, Andronova VL, Moiseeva ED, Nikitin CA, Golovkin MV, Galegov GA, Grokhovsky SL, Gursky GV. Complex of the herpes simplex virus type 1 origin binding protein UL9 with DNA as a platform for the design of a new type of antiviral drugs. J Biomol Struct Dyn. 2014;32(9):1456-73. Epub Jul. 24, 2013.*

Cullen BR. "Update on HSV Research". Sep. 2014. https://sites.duke.edu/cullenlaboratory/current-research/herpes-research/update-on-hsv-research/.*

Balliet JW, Min JC, Cabatingan MS, Schaffer PA. Site-directed mutagenesis of large DNA palindromes: construction and in vitro characterization of herpes simplex virus type 1 mutants containing point mutations that eliminate the oriL or oriS initiation function. J Virol. Oct. 2005;79(20):12783-97.*

Balliet JW, Schaffer PA. Point mutations in herpes simplex virus type 1 oriL, but not in oriS, reduce pathogenesis during acute infection of mice and impair reactivation from latency. J Virol. Jan. 2006;80(1):440-50.*

Summers BC, Leib DA. Herpes simplex virus type 1 origins of DNA replication play no role in the regulation of flanking promoters. J Virol. Jul. 2002;76(14):7020-9.*

Bazhulina NP, Surovaya AN, et. al. Complex of the herpes simplex virus type 1 origin binding protein UL9 with DNA as a platform for the design of a new type of antiviral drugs. J Biomol Struct Dyn. 2014;32(9):1456-73. Epub Jul. 24, 2013.*

Mali et al., 2013, Cas9 as a versatile tool for engineering biology, Nat Meth 10(10):957.

McCombs & Owen, 2015, Antibody drug conjugates: design and selection of linker, payload and conjugation chemistry, AAPS J 17(2):339-51.

Munger et al., 2004, Mechanisms of human papillomavirus-induced oncogenesis, J Virol 78(21):11451-11460.

Naito et al., 2014, CRISPRdirect: software for designing CRISPR/Cas guide RNA with reduced off-target sites, Bioinformatics.

Naito, 2015, CRISPR direct: software for designing CRISPR/Cas guide RNA with reduced off-target sites, Bioinformatics 31:1120-1123.

Nishimasu et al., 2014, Crystal structure of Cas9 in complex with guide RNA and target DNA, Cell 156:935-949.

(56) References Cited

OTHER PUBLICATIONS

Nozaki et al., 2003, Enhancement of ultrasound-mediated gene transfection by membrane modification, J Gene Med 5(12):1046-1055.
Prausnitz & Langer, 2008, Transdermal drug delivery, Nat Biotech 26(11):1261-1268.
Prausnitz et al., 1993, Electroporation of mammalian skin: a mechanism to enhance transdermal drug delivery, PNAS 90:10504-10508.
Price, 2015, Cas9-mediated targeting of viral RNA in eukaryotic cells, PNAS, 1112(19):6164-6169.
Puren et al., 2010, Laboratory operations, specimen processing, and handling for viral load testing and surveillance, J Inf Dis 201(Suppl 1):S27-36.
Qi et al., 2013, Repurposing CRISP as an RNA-guided platform for sequence-specific control of gene expression, Cell 152:1173-1183.
Qu et al., 2013, Zinc-finger-nucleases mediate specific and efficient excision of HIV-1 proviral DAN from infected and latently infected human T cells, Nucl Ac Res 41(16):7771-7782.
Ran et al., 2015, In vivo genome editing using *Staphylococcus aureus* Cas9, Nature 520(7546):186-191.
Rojanasakul et al., 1994, Targeted gene delivery to alveolar macrophages via Fc receptor-mediated endocytosis, Pharm Res 11(12)1731-6.
Ruf et al., 2000, Epstein-Barr virus small RNAs potentiate tumorigenicity of Burkitt lymphoma cells independently of an effect on apoptosis, J Virol 74(21):10223-10228.
Russell, 2015, Engineering herpes simplex viruses by infection-transfection methods including recombination site targeting by CRISPR/Cas9 nuclease, J Virol Meth 213:18-25.
Schiffer et al., 2013, Predictors of hepatitis B cure using gene therapy to deliver DNA cleavage enzymes: a mathematical modeling approach, PLoS Comp Biol 9(7):e1003131.
Schiffer, 2012, Targeted DNA mutagenesis for the cure of chronic viral infections, J Virol 88(17):8920-8936.
Schwank et al., 2013, Functional repair of CFTR by CRISPR/Cas9 in intestinal stem cell organoids of cystic fibrosis. patients, Cell Stem Cell 13(6):653-8.
Silva et al., 2011, Meganucleases and other tools for targeted genome engineering, Curr Gene Ther 11(1):11-27.
Smith, 2007, Perspectives on transdermal ultrasound mediated drug delivery, Int J Nanomed 2(4):585-594.
Sternberg et al., 2014, DNA interrogation by the CRISPR RNA-guided endonuclease Cas9, Nature 507(7490):62-67.
Surovaya, 2010, Complex of the herpes simplex virus initiator protein UL9 with DNA as a platform for the design of a new type of antiviral drugs, Biophysics 55(2):204-214.
Terns et al., 2011, CRISPR-based adaptive immune systems, Curr Op Microb 14:321-327.
Tsutsui et al., 2004, The use of microbubbles to target drug delivery, Cardiovasc Ultrasound 2:23.
Turner, 2011, Administration of substances to laboratory animals: routes of administration and factors to consider, J Am Assoc Lab Anim Sci 50(5):600-613.
Wah, et al., 1998, Structure of FokI has implications for DNA cleavage, PNAS 95:10564-10569.
Wang, 2014, RNA-guided endonuclease provides a therapeutic strategy to cure latent herpesviridae infection, PNAS 111(36):13157-13162.
Wang et al., 2013, One-step generation of mice carrying mutations in multiple genes by CRISPR/Cas-mediated genome engineering, Cell 153:910-918.
Westergaard et al., 2001, Modulation of keratinocyte gene expression and differentiation by PPAR-selective ligands and tetradecyltheioacetic acid, J Invest Dermatol 116(5):702-12.
White, 2015, The CRISPR/Cas9 Genome Editing Methodology as a Weapon Against Human Viruses, Disc Med 19(105):255-262.
Wiedenheft et al., 2012, RNA-guided genetic silencing systems in bacteria and archaea, Nature 482:331-338.
Woodland, 2004, Jump-starting the immune system: prime-boosting comes of age, Trends Immunol 25(2):98.
Wu & Wu, 1987, Receptor-mediated in vitro gene transformation by a soluble DNA carrier system, J Biol Chem 262:4429.
Xiao et al., 2013, Chromosomal deletions and inversions mediated by TALENS and CRISPR/Cas in zebrafish, Nucl Acids Res 1-11.
Xue et al., 2014, Efficient gene knock-out and knock-in with transgenic Cas9 in *Drosophila*, G3 4:925-929.
Yamagami, 2011, Hepatic artery-targeting guidewire technique during transjugular intrahepatic portosystemic shunt, Br J Radiol 84(1000):315-318.
Yang et al., 1990, In vivo and in vitro gene transfer to mammalian somatic cells by particle bombardment, PNAS 87:9568-9572.
Yang et al., 2013, One-step generation of mice carrying reporter and conditional alleles by CRISPR/Cas-mediated genome enginneering, Cell 154:1370-1379.
Yuan, 2015, Efficiently editing the vaccina virus genome by using the CRISPR-Cas9 system, J Vir 89(9):5176-5179.
Zensi et al., 2009, Albumin nanoparticles targeted with Apo E enter the CNS by transcytosis and are delivered to neurons, J Control Release 137:78-86.
Zhang et al., 2014, Gene transfection in complex media using PCBMAEE-PCBMA copolymer with both hydrolytic and zwitterionic blocks, Biomaterials 35(27):7909-18.
Zhang et al., 2015, Development of an efficient electroporation method for iturin A-producing Bacillus subtilis ZK, Int J Mol Sci 16:7334-7351.
Zheng & Baker, 2006, Papillomavirus genome structure, expression, and post-transcriptional regulation, Front Biosci 11:2286-2302.
Belfort & Roberts, 1997, Homing endonucleases: keeping the house in order, Nucleic Acids Res 25(17):3379-3388.
Bernard, 2007, Gene expression of genital human papillomaviruses and considerations on potential antiviral approaches. Antivir.Ther. 7:219-237.
Bessis et al., 2004, Immune responses to gene therapy vectors: influence on vector function and effector mechanisms, Gene Ther 11:S10-S17.
Bhaya et al., 2011, CRISPR-Cas systems in bacteria and archea: versitle small RNAs for adaptive defense and regulation, Annu Rev Genet 45:273-297.
Bi et al., 2014, High-efficiency targeted editing of large viral genomes by RNAguided nucleases, PLoS Pathog 10:e1004090.
Bloom, 2013, Inactivatoin of hepatitis B virus replication in cultured cells and in vivo with engineered transcription activator-like effector nucleases, Mol Ther 21:1889-1897.
Carter, 2011, Introduction to current and future protein therapeutics: a protein engineering perspective, Exp Cell Res 317:1261-1269.
Casselman, 1954, Guided catheterization of hepatic veins and estimation of hepatic blood flow by the bromsulphalein method in normal dogs, J Physiol 124(1):173-182.
Chang et al., 2013, Genome editing with RNA-guided Cas9 nuclease in zebrafish embryos, Cell Res 23:465-472.
Chen et al., 2013, Dynamic Imaging of Genomic Loci in Living Human Cells by an Optimized CRISPR/Cas System. Cell 155:1479-1491.
Cong et al., 2013, Multiplex Genome Engineering Using CRISPR/Cas Systems, Science 339:819-823.
Cox et al., 2015, Therapeutic genome editing: prospects and challenges, Nat Med 21(2):121-131.
Davis et al., 2008, Nanotherapeutic particles: an emerging treatment modality for cancer, Nat Rev Drug Disc 7. (9):771-782.
DeGroot, 2009, Reducing risk, improving outcomes: bioengineering less immunogenic protein therapeutics, Clin Imm 131:189-201.
Deng et al., 2009, Hepatitis B virus as a gene delivery vector activating foreign antigenic T cell response that abrogates viral expression in mouse models, Hepatology 50(5):1380.
Ebina et al., 2013, Harnessing the CRISPR/Cas9 system to disrupt latent HIV-1 provirus, Sci Rep 3:2510.
Gao et al., 2007, Nonviral gene delivery: what we know and what is next, AAPS J 9(1):E92-E104.
Georgieva et al., 2014, Smuggling drugs into the brain: an overview of ligands targeting transcytosis for drug delivery across the blood-brain barrier, Pharmacuetics 6(4):557-583.

(56) References Cited

OTHER PUBLICATIONS

Gilbert et al., 2013, CRISPR-mediated modular RNA-guided regulation of transcription in eukaryotes, Cell 154:442-451.
Glatzel et al., 2000, Adenoviral and adeno-associated viral transfer of genes to the peripheral nervous system PNAS 97(1):442-447.
Gomaa, 2014, Programmable removal of bacterial strains by use of genome-targeting CRISPR-Cas systems, MBio 5:e00928.
Green et al., 2013, Epstein-Barr virus infection and posttransplant lymphoproliferative disorder, Am J Transplant 13(Suppl 3):41-54.
Guo et al., 2012, Recent advances in non-viral vectors for gene delivery, Acc Chem Res 45(7):971-979.
Gupta et al., 2001, Single chain Fv: a ligand in receptor-mediated gene delivery, Gene Ther 8(8):586-92.
Harrison et al., 2014, A CRISPR view of development, Genes and Development 28:1859-1872.
Hein et al., 2009, Click chemistry, a powerful tool for pharmaceutical sciences, Pharm Res 25(10):2216-2230.
Horvath et al., 2010, CRISPR/Cas, the immune system of bacteria and archaea, Science 327:167-170.
Hoshino et al., 2008, The number of herpes simplex virus-infected neurons and the number of viral genome copies per neuron correlate with latent viral load in ganglia, Virology 372(1):56-63.
Hsu et al., 2014, Development and applications of CRISPR-Cas9 for genome engineering, Cell 157:1262.
Hsu, 2013, DNA targeting specificity of RNA-guided Cas9 nucleases, Nature Biotechnology 31(9):827-832.
Hu et al., 2014, RNA-directed gene editing specifically eradicates latent and prevents new HIV-1 infection, PNAS 111(31):11461-6.
Hu, 2014, RNA-directed gene editing specifically eradicates latent and prevents new HIV-1 infection, PNAS 111:11461-11466.
Hui, 1996, High-efficiency loading transfection and fusion of cells by electroporation in two-phase polymer systems, Biophys J 71:1123-1130.
Hwang et al., 2013, Efficient genome editing in zebrafish using a CRISPR-Cas system, Nat Biotech 31:227-229.
International Search Report and Written Opinion dated Aug. 29, 2016 for International Application No. PCT/US2016/034700 with International filing date May 27, 2016 (15 Pages).
International Search Report and Written Opinion dated Sep. 22, 2016, for International Patent Application PCT/US2016/034638 with International Filing Date May 27, 2016 (13 pages).
International Search Report and Written Opinion of the International Searching Authority dated Jul. 15, 2016 for International Application No. PCT/US2016/025517 (15 Pages).
International Search Report and Written Opinion of the International Searching Authority dated Sep. 6, 2016 for International Application No. PCT/US2016/034606 (16 Pages).
Jinek et al., 2013, RNA-programmed genome editing in human cells, Elife 2:e00471.
Jinek, 2012, A programmable dual-RNA-guided DNA endonuclease in adaptive bacterial immunity, Science 337:816-821.
Joung & Sander, 2013, TALENs: a widely applicable technology for targeted genome editing, Nat Rev Mol Cell Bio 14:49-55.
Kennedy, 2014, Suppression of Hepatitis B virus DNA accumulation in chronically infected cells using a bacterial CRISPR/Cas RNA-guided DNA endonuclease, Virol 476:1-22.
Labrou, 2010, Random mutagenesis methods for in vitro directed enzyme evolution, Curr Protein Pep Sci 11(1):91-100.
Lee et al., 2001, Enhancing transfection efficiency using polyethylene glycol grafted polyethylenimine and fusogenic peptide, Biotechnol Bioprocess Eng 6:269-273.
Liu et al., 2004, CMV enhancer/human PDGF-beta promoter for neuron specific transgene expression, Gene Ther 11(1):52-60.
Liu et al., 2006, Encapsulated ultrasound microbubbles: therapeutic application in drug/gene delivery, J Controlled Release 114(1):89-99.
Lorenceau et al., 2005, Generation of Polymerosomes from Double-Emulsions, Langmuir 21(20):9183-6.
Ma, 2013, A guide RNA sequence design platform for the CRISPR/Cas9 system for model organisms, Biomed Res Int 270805.
Machine translation of CN 10391136 A generated on Dec. 21, 2015, by the web site of the European Patent Office (7 pages).
Mali et al, 2013, RNA-guided human genome engineering via Cas9, Science 339:823-826.
Bazhulina, 2014, Complex of the herpes simplex virus type 1 origin binding protein UL9 with DNA as a platform for the design of a new type of antiviral drugs, J Biomol Struct Dyn 32(9):1456-73.
Bi, 2014, High-efficiency targeted editing of large viral genomes by RNA-guided nucleases, PLoS Pathog 10(5):e1004090.
Bitinaite, 1998, FokI dimerization is required for DNA cleavage, PNAS 95(18):10570-10575.
Dampier, 2014, HIV excision utilizing CRISPR/Cas9 technology: attacking the proviral quasispecies in reservoirs to achieve a cure, MOJ Immunology 1(4):00022.
Duellman, 2009, Phosphorylation sites of Epstein-Barr Virus EBNA1 regulate its function, J Gen Virol. 90(9):2251-9.
Favre, 2003, Latent hepatitis B virus (HBV) infection and HBV DNA integratoin is associated with further transformation of hepatoma cells in vitro, Altex 20:131-142.
Gaj, 2013, ZFN, TALEN, and CRISPR/Cas-based methods for genome engineering, Trends Biotech 31(7):397-405.
Griffin, 2013, Human papillomavirus infection is inhibited by host autophagy in primary human keratinocytes, Virology 437(1):12-19.
Grosse, 2011, Meganuclease-mediated inhibition of HSV1 infection in cultured cells, Mol Ther 19(4):694-702.
Hay, 2007, Chapter 10: Alphaherpesvirus DNA Replication, Human Herpesviruses: Biology, Therapy, and Immunoprophylaxis, Arvin et al., Eds. Cambridge University Press (13 Pages).
Hu, 2014, Disruption of HPV16-E7 by CRISPR/Cas System Induces Apoptosis and Growth Inhibition in HPV16 Positive Human Cervical Cancer Cells, Biomed Res Int 31(3):209-9.
Huang, 1994, The activity of the Pseudorabies virus latency-associated transcript promoter is dependent on its genomic location in Herpes Simplex Virus recombinatnats as well as on the type of cell infected, J Virol 68(3):1972-1976.
International Search Report and Written Opinion dated Dec. 15, 2016, for application PCT/US16/53960, with International filing date Sep. 27, 2016 (11 pages).
International Search Report and Written Opinion dated Dec. 19, 2016, for PCT/US2016/054138 (9 Pages).
International Search Report and Written Opinion dated Sep. 28, 2016, for International Patent Application No. PCT/US2016/034627, with International Filing Date May 27, 2016 (23 pages).
Jafari, 2012, Nonviral approach for targeted nucleic acid delivery, Curr Med Chem 19:197-208.
Kennedy, 2003, EBNA1, a Bifunctional Transcription Activator, Mol Cell Biol 23(19):6901-6908.
Kennedy, 2014, Inactivation of the Human Papillomavirus E6 or E7 Gene in Cervical Carcinoma Cells by Using a Bacterial CRISPR/Cas RNA-Guided Endonuclease, J Virol 88(20):11965-11972.
Kim, 1994, Chimeric restriction endonuclease, PNAS 91:883-887.
Kim, 2014, Highly efficient RNA-guided genome editing in human cells via delivery of purified Cas9 ribonucleoproteins, Genome Res 24(6):1012-1019.
Kuchta, 2012, Structural modelling and mutagenesis of Human Cytomegalovirus alkaline nuclease UL98, J Gen Virl 93(1):130-138.
Li, 1992, Functional domains in Fok I restriction endonuclease, PNAS 89:4275-4279.
Liao, 2015, Use of the CRISPR/Cas9 system as an intracellular defense against HIV-1 infection in human cells, Nat Comm 6:6413.
Lin, 2001, Differential Expression of Tissue-Specific Promoters by Gene Gun, Brit J Derm 144(1):34-39.
Lin, 2014, The CRISPR/Cas9 system facilitates clearance of the intrahepatic HBV templates in vivo, Mol Ther Nucleic Acids 3:e186.
Marusawa, 2000, Latent hepatitis B virus infection in healthy individuals with antibodies to hepatitis core B antigen, Hepatology 31(2):488-495.
Masaoka, 2016, Characterization of the C-Terminal nuclease domain of Herpes Simplex Virus pUL15 as a target of nucleotidyltransferase Inhibitors, Biochem 55(5):809-19.

(56) References Cited

OTHER PUBLICATIONS

Qi, 2014, A versatile framework for microbial engineering using synthetic non-coding RNAs, Nat Rev Mic 12:341-354.
Qu, 2014, Zinc finger nuclease: a new approach for excising HIV-1 proviral DNA from infected human T cells, Mol Biol Rep 41:5819-5827.
Quarleri, 2014, Core promoter: a critical region where the hepatitis B virus maeks decisions, World J Gast 20(2):425-435.
Seeger, 2014, Targeting Hepatitis B Virus with CRISPR/Cas9, Mol Ther Nucleic Acids 3:e216.
Selvarajan, 2013, The structure of the herpes simplex virus DNA-packaging terminase pUL15 nuclease domain suggests an evolutionary lineage among eukaryotic and prokaryotic viruses, J Virol 87(12):7140-8.
Wang, 2014, State-of-the-art human gene therapy: Part I. Gene delivery technologies, Discov Med 18(97):67-77.
Wang, 2014, State-of-the-art human gene therapy: Part II. Gene therapy strategies and applications, Discov Med 18(98):151-161.
Weller, 2013, The DNA helicase-primase complex as a target for herpes viral infection, Expert Op Ther Targets 17(10):1119-32.
Young, 2003, Epstein-Barr Virus and oncogenesis: from latent genes to tumors, Oncogene 22(33):5108-5121.
Yu, 2015, Disruption of human papillomavirus 16 E6 gene by clustered regularly interspaced short palindromic repeat/Cas system in human cervical cancer cells, Onco Targets Ther 2014 8:37-44.
Zhen, 2014, In vitro and in vivo growth suppression of human papillomavirus 16-positive cervical cancer cells by CRISPR/Cas9, Biochem Biophys Res Comm 4(8):1422-1426.

\* cited by examiner

COMPOSITIONS AND METHODS TO TREAT HERPES SIMPLEX VIRUS INFECTIONS

CROSS-REFERENCE TO RELATED APPLICATION

This application claims the benefit and priority of U.S. Provisional Application No. 62/168,259, filed May 29, 2015, the contents of which are incorporated by reference.

TECHNICAL FIELD

The invention generally relates to treatment of viral infections and cleaving foreign nucleic acids in cells.

BACKGROUND

Herpes simplex virus (HSV) is a commonly used reference to two members of the Herpesviridae family, herpes simplex virus 1 (HSV-1) and herpes simplex virus 2 (HSV-2). An active HSV-1 infection causes mainly oral herpes, which may result in small blisters around face or mouth. An active HSV-2 infection generally affects the genital area, causing blisters that can break open and result in small ulcers. Tingling or shooting pains may occur before the blisters appear. Worldwide, about 90% of people are infected with one or both of HSV-1 and HSV-2 with HSV-1 infection much more prevalent than HSV-2 infection. About 65% of persons in the United States have antibodies to HSV-1 and about 16% of Americans between the ages of 14 and 49 are infected with HSV-2.

HSV-1 and 2 have the ability to lie dormant within a cell indefinitely in a latent infection and not be fully eradicated even after treatment. The result is that the virus can reactivate and begin producing large amounts of viral progeny without the host being infected by any new outside virus. In the latent state, the viral genome persists within the host cells as episomes; stabilized and floating in the cytoplasm or nucleus.

There is no cure for HSV and, once infected, a host carries the herpes virus indefinitely, even when not expressing symptoms in an active infection or outbreak. While various antiviral treatments are available, they generally are directed to interrupting the replicating cycle of the virus and, therefore, prove ineffective at eradicating latent infections. Because latent infections can evade immune surveillance and reactivate the lytic cycle at any time, there is a persistent risk to an infected individual of outbreak and the pain and suffering associated with it. The majority of antiviral drug development has been focused on protein targets but such approaches have not been successful in eradicating HSV.

SUMMARY

The invention provides compositions and methods for selectively treating HSV infection using a guided nuclease system that targets a specific region of the HSV genome such as oriS, UL9, RL2, or LAT. Methods of the invention may be used to remove even latent HSV genetic material from a host organism, without interfering with the integrity of the host's genetic material. A nuclease may be targeted to HSV nucleic acid where it can then disrupt the nucleic acid, thereby interfering with viral replication or transcription or even excising the viral genetic material from the host genome. Through use of a sequence-specific targeting moiety directed to HSV, the nuclease may be specifically targeted to remove only the HSV nucleic acid without acting on host material whether the viral nucleic acid exists as a particle within the cell or is integrated into the host genome. A sequence-specific moiety can include a guide RNA that targets viral genomic material for destruction by the nuclease and does not target the host cell genome. In some embodiments, a CRISPR/Cas9 nuclease and guide RNA (gRNA) that together target and selectively edit or destroy viral genomic material is used. CRISPR (clustered regularly interspaced short palindromic repeats) is a naturally-occurring element of the bacterial immune system that protects bacteria from phage infection. The guide RNA localizes the CRISPR/Cas9 complex to a HSV target sequence, such as oriS, UL9, RL2, or LAT. Binding of the complex localizes the Cas9 endonuclease to the HSV genomic target sequence causing breaks in the viral genome.

The guided nuclease system may be introduced into an infected host transdermally through application of, for instance, a topical solution. Topical solutions may be applied directly to infected tissue.

The sequence specific moiety can target other nuclease systems to HSV nucleic acid including, for example, zinc finger nucleases, transcription activator-like effector nucleases (TALENs), meganucleases, or any other system that can be used to degrade or interfere with HSV nucleic acid without interfering with the regular function of the host's genetic material.

Aspects of the invention include a composition for treatment of a herpes simplex virus (HSV) infection. The composition comprises a vector encoding a nuclease and a sequence-specific targeting moiety complementary to HSV nucleic acid and capable of directing the nuclease to the HSV nucleic acid.

In certain embodiments, the HSV nucleic acid may comprise one or more of the following regions: origin of replication S (oriS), long unique region 9 (UL9), or long repeat region 2 (RL2). The composition may be configured to be administered transdermally, for example, through a topical solution. The nuclease may be a zinc-finger nuclease, a transcription activator-like effector nuclease, and a meganuclease.

In various embodiments, the nuclease may a Cas9 endonuclease and the sequence-specific binding module may comprise a guide RNA that specifically targets a portion of a viral genome. Compositions of the invention may be packaged for delivery to a human patient.

In certain embodiments, the targeting sequence may be a guide RNA that has no match >60% within a human genome.

The vector may include a retrovirus, a lentivirus, an adenovirus, a herpesvirus, a poxvirus, an alphavirus, a vaccinia virus, an adeno-associated viruses, a plasmid, a nanoparticle, a cationic lipid, a cationic polymer, metallic nanoparticle, a nanorod, a liposome, microbubbles, a cell-penetrating peptide, or a liposphere.

In certain aspects, the invention includes a method for treating an HSV infection including the step of introducing into a cell of a host, a vector encoding a nuclease and a sequence-specific targeting moiety complementary to HSV nucleic acid. Additional steps include causing the sequence-specific targeting moiety to target the nuclease to the HSV nucleic acid and to cleave the HSV nucleic acid.

The HSV nucleic acid can include a portion of or all of one or more genomic regions including an origin of replication S (oriS), long unique region 9 (UL9) or long repeat region 2 (RL2). Methods of the invention may include transdermally administering the vector to the host and transdermal administration may include applying a topical solution comprising the vector.

The nuclease may be a zinc-finger nuclease, a transcription activator-like effector nuclease, or a meganuclease. In certain embodiments, the nuclease may include a Cas9 endonuclease and the sequence-specific binding module may include a guide RNA that specifically targets a portion of a viral genome.

In various methods of the invention, the host may be a living human subject and the steps may be performed in vivo. The targeting sequence may be a guide RNA and have no match >60% within a human genome.

In certain methods, the vector may include a retrovirus, a lentivirus, an adenovirus, a herpesvirus, a poxvirus, an alphavirus, a vaccinia virus, an adeno-associated viruses, a plasmid, a nanoparticle, a cationic lipid, a cationic polymer, metallic nanoparticle, a nanorod, a liposome, microbubbles, a cell-penetrating peptide, or a liposphere.

The presented methods allow for HSV genome editing or destruction, which results in the inability of the HSV virus to proliferate without adversely affecting a host's uninfected cells. Compositions and methods of the invention can accordingly be used to treat an HSV infection through targeted disruption of HSV genomic function or by digestion of viral nucleic acid via one or multiple breaks caused by targeting sites such as oriS, UL9, RL2, or LAT for endonuclease action in the HSV genome.

In preferred aspects, the invention provides a composition for treatment of a herpes simplex virus (HSV) infection. The composition includes a ribonucleoprotein that includes: a nuclease; and a sequence-specific targeting moiety complementary to HSV nucleic acid and capable of directing the nuclease to the HSV nucleic acid. The HSV nucleic acid may include an origin of replication S (oriS) region, a long unique region 9 (UL9), a long repeat region 2 (RL2), or a combination thereof. Preferably, the nuclease comprises a Cas9 endonuclease and the sequence-specific binding module comprises a guide RNA that specifically targets a portion of a viral genome. The targeting sequence is a guide RNA and has no match >60% within a human genome.

The composition may be configured to be administered transdermally. In some embodiments, the composition includes a pharmaceutically acceptable carrier for topical application to infected tissue.

DETAILED DESCRIPTION

Embodiments of the invention relate to compositions and methods for treating HSV infections including HSV-1 and HSV-2 infections using guided nuclease systems targeted to specific regions of the HSV genome such as RL2, LAT, UL9, or OriS. Compositions of the invention disrupt HSV viral nucleic acid in host cells through nuclease activity without affecting the host's genome. Through disruption of the HSV genome in infected host cells, methods and compositions of the invention may eradicate even latent HSV infections.

Additionally or alternatively, embodiments of the invention related to methods for treating cytomegalovirus (CMV). Methods of the invention are used to incapacitate or disrupt CMV within a cell, a tissue, or a patient by systematically causing large or repeated insertions or deletions in the CMV genome, reducing the probability of reconstructing the full genome. The insertions or deletions in the genome incapacitates or destroys the virus, thus treating CMV. In some embodiments, the nuclease may be a CRISPR/Cas9 complex. In some embodiments, the nuclease is guided by a sequence, such as a guided RNA. In some embodiments, tissues, such as organs are treated with the nuclease prior to transplantation. In some embodiments, a transplant donor or recipient are treated before and after a transplantation surgery. In some embodiments, a patient infected with CMV is treated with the nuclease.

Figure 1:
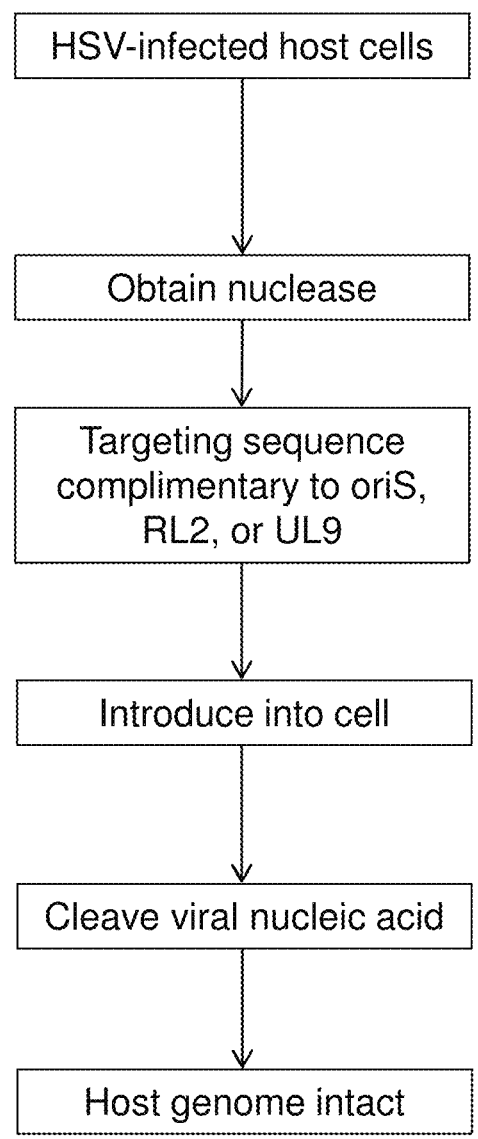
FIG. 1 diagrams a method of targeting an HSV infection.

FIG. 1 diagrams a method of targeting an HSV infection. The method includes obtaining a targetable nuclease (e.g., as a protein or a gene for a nuclease). Any suitable nuclease can be used such as ZFN, TALENs, or meganucleases. In a preferred embodiment, the nuclease is Cas9. A sequence is provided that targets the nuclease to specific targets on the HSV genome such as oriS, UL9, RL2, or LAT. The nuclease gene and encoded gRNAs may be provided in a DNA vector, such as a plasmid or an adenovirus based vector, and the vector may further optionally include a promoter. That composition is then introduced into the HSV-infected cells. Any suitable transfection or delivery method may be used. Once in the cell, the genes are expressed and the Cas9 enzyme uses the gRNA to target, and cleave, the HSV genome. Since the gRNA is specific to the HSV genome with no match to the human genome according to methods and criteria described herein, the method leaves the host genome intact and does not interfere with normal human genetic function.

Discussion of HSV as well as regions for targeting can be found in Summers, et al., 2002, Herpes Simplex Virus Type 1 Origins of DNA Replication Play No Role in the Regulation of Flanking Promoters, J Virol., 76(14); Eom, et al., 2003, Replication-initiator protein (UL9) of the herpes simplex virus 1 binds NFB42 and is degraded via the ubiquitin—proteasome pathway, Proc Natl Acad Sci U S A, 100(17): 9803-9807; McGeoch, et al., 1991, Comparative sequence analysis of the long repeat regions and adjoining parts of the long unique regions in the genomes of herpes simplex viruses types 1 and 2, J Gen Virol., 72 (Pt 12):3057-75; the contents of each of which are incorporated by reference in their entirety for all purposes.

Figure 2:
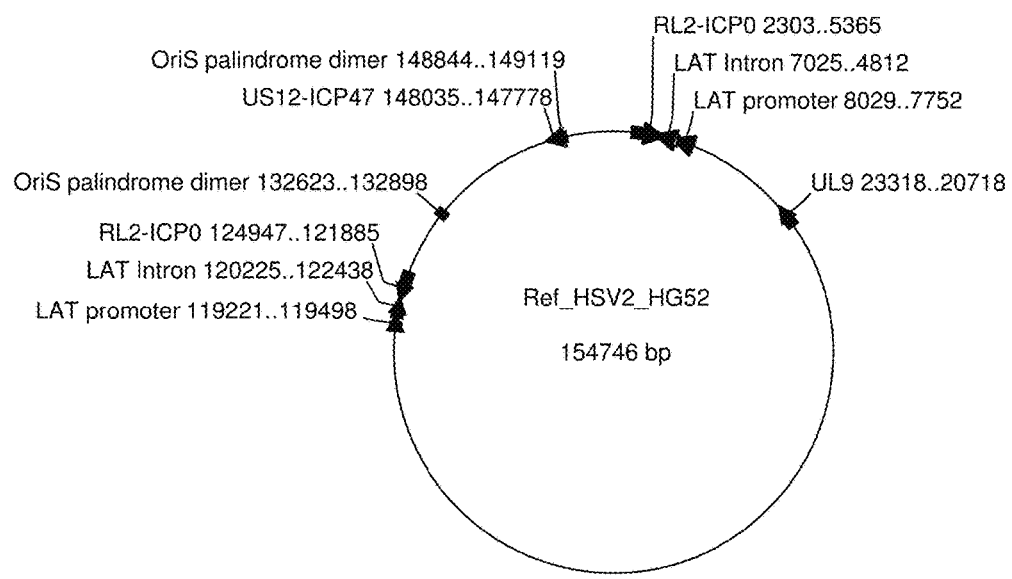
FIG. 2 is a map of an HSV genome.

FIG. 2 shows the HSV genome and the HSV oriS palindrome dimer (oriS), RL2-ICP0 (RL2), LAT Intron (LATi), LAT promoter (LATp), UL9, and US12 genes which may be targeted by CRISPR guide RNAs.

Figure 3:
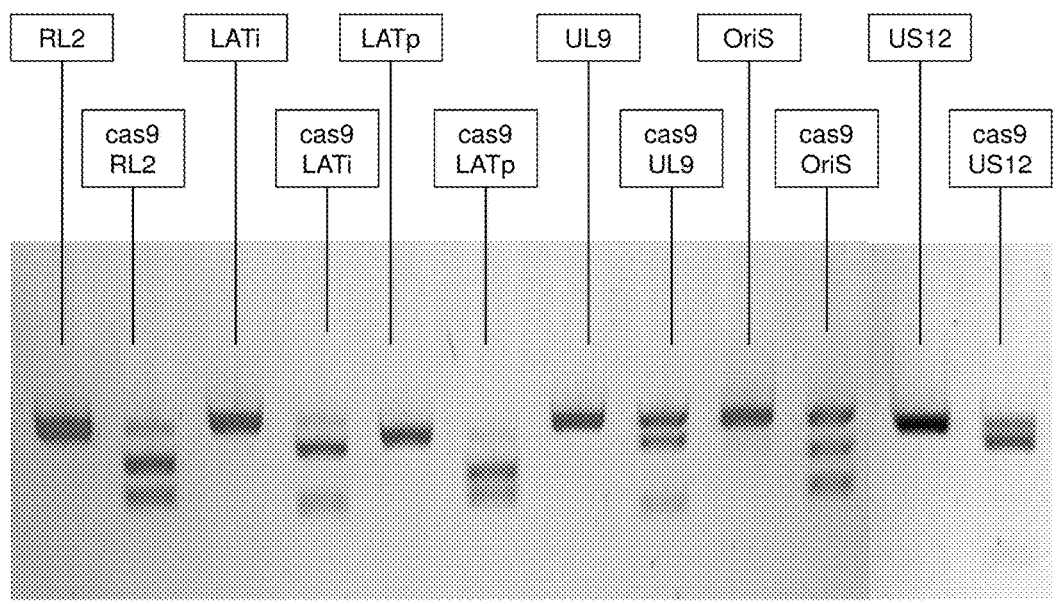
FIG. 3 shows amplicons of HSV genomic regions before and after digestion with cas9. The lanes of the gel show genomic DNA size bands for cells treated with the RL2, LATi, LATp, UL9, OriS, and US12 guide sequences with and without Cas9.

FIG. 3 shows amplicons of HSV genomic regions before and after digestion with cas9 and corresponding guide RNAs. T7 in vitro transcription was used to produce the complete guide RNA with scaffold for RL2, LATi, LATp, UL9, oriS, and US12. Flanking regions of the genome targets were PCR amplified from HSV2 strain G genomic DNA (from ATCC). Cas9 protein (from PNA Bio), guide RNA and target DNA were mixed and incubated for in vitro endonuclease assay. High endonuclease activities were revealed by DNA gel electrophoresis of the digested DNA as shown in FIG. 3 which shows PCR amplicons of RL2, LATi, LATp, UL9, oriS, and US12 before and after digestion with cas9 and the guide RNA targeting each respective genomic region.

Figure 37:
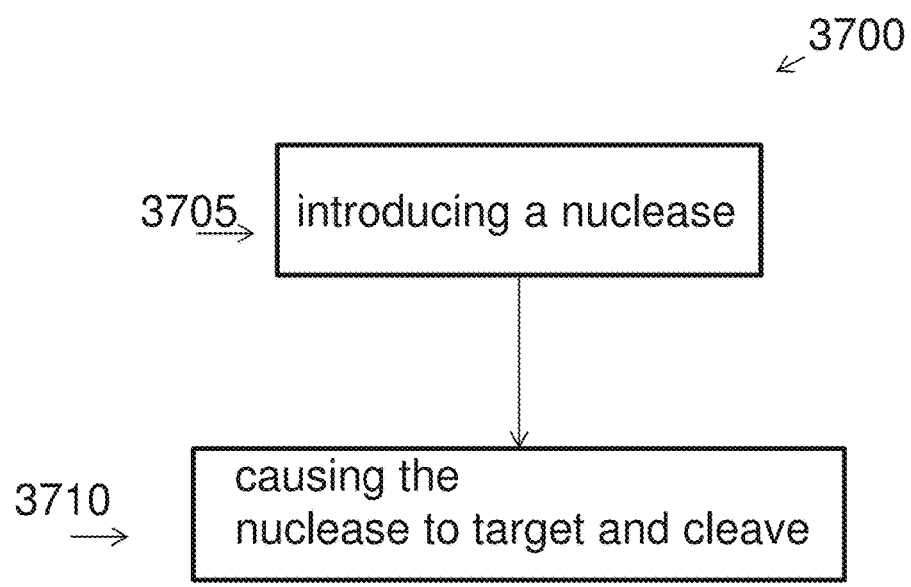
FIG. 37 depicts a flow chart of embodiments of the invention for targeting CMV.
Figure 38:
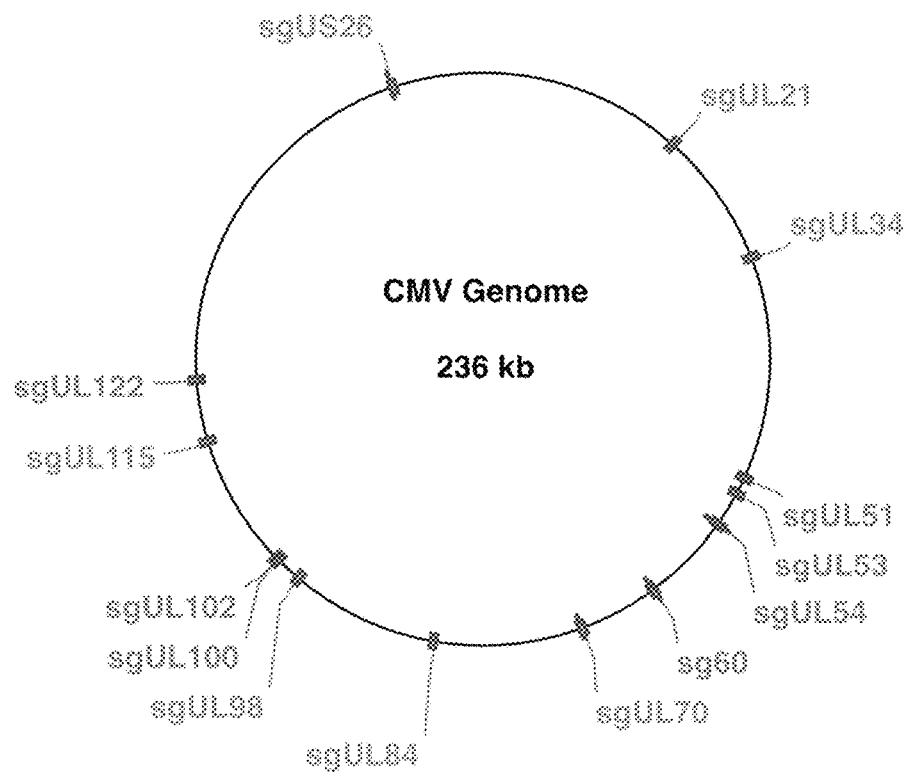
FIG. 38 is a map of a CMV genome.
Figure 39:
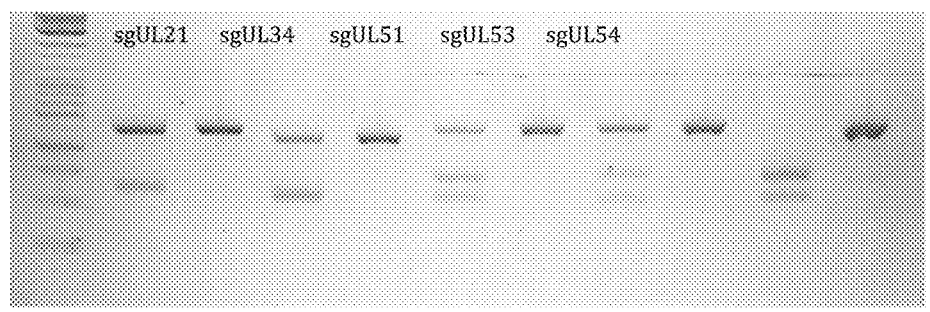
FIG. 39 depicts results from an in vitro CRISPR endonuclease assay, showing PCR amplicons from CMV genome and the corresponding products from in vitro CRISPR digestion (shown in pairs).
Figure 40:
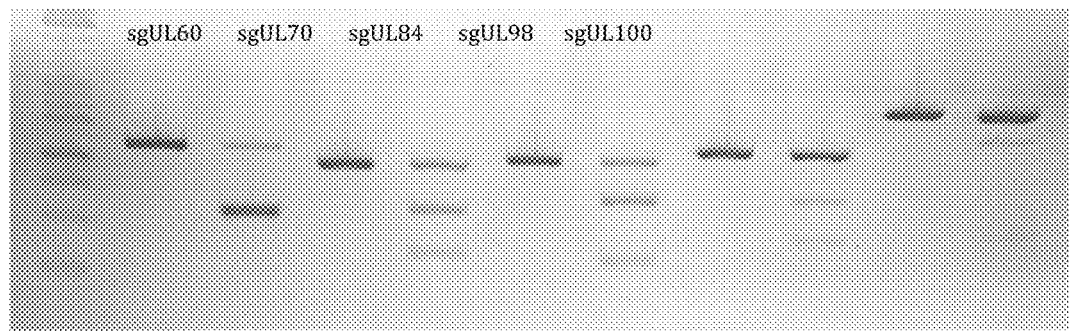
FIG. 40 depicts results from an in vitro CRISPR endonuclease assay, showing PCR amplicons from CMV genome and the corresponding products from in vitro CRISPR digestion (shown in pairs).
Figure 41:
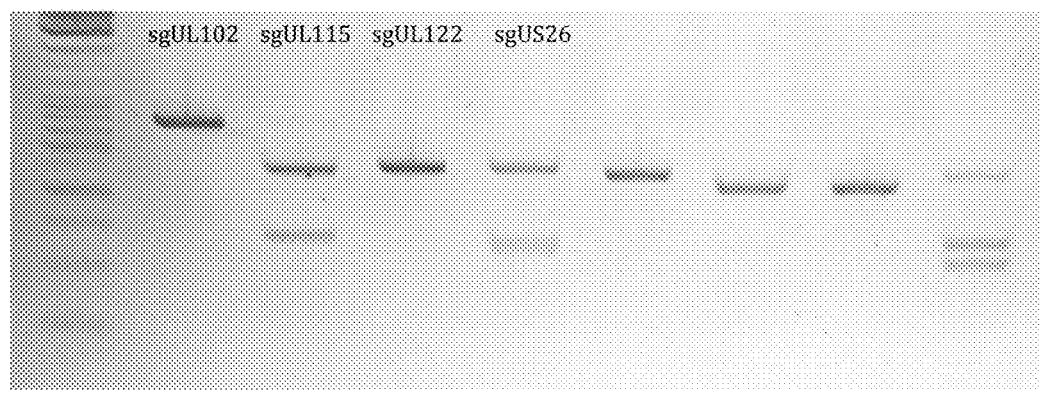
FIG. 41 depicts results from an in vitro CRISPR endonuclease assay, showing PCR amplicons from CMV genome and the corresponding products from in vitro CRISPR digestion (shown in pairs).

FIG. 37 depicts a flow chart of embodiments of the invention for targeting CMV. In general, the method 100 comprises introducing a nuclease 105 that targets the CMV genome. The nuclease can be introduced into an organ or a pregnant woman. The organ or the fetus can be suspected of having a CMV infection. The method further comprises causing the nuclease to target and cleave 110 a CMV nucleic acid. The nuclease is able to bind to and alter the CMV genome.

i. Treating Infected Cell

Cells may be treated with a nuclease encoded in a nucleic acid (e.g., delivered as mRNA or a plasmid) or delivered in active form. Where the nuclease is a CRISPR-associated protein such as Cas9, an active ribonucleoprotein (RNP) may be delivered to the cells.

Figure 42:
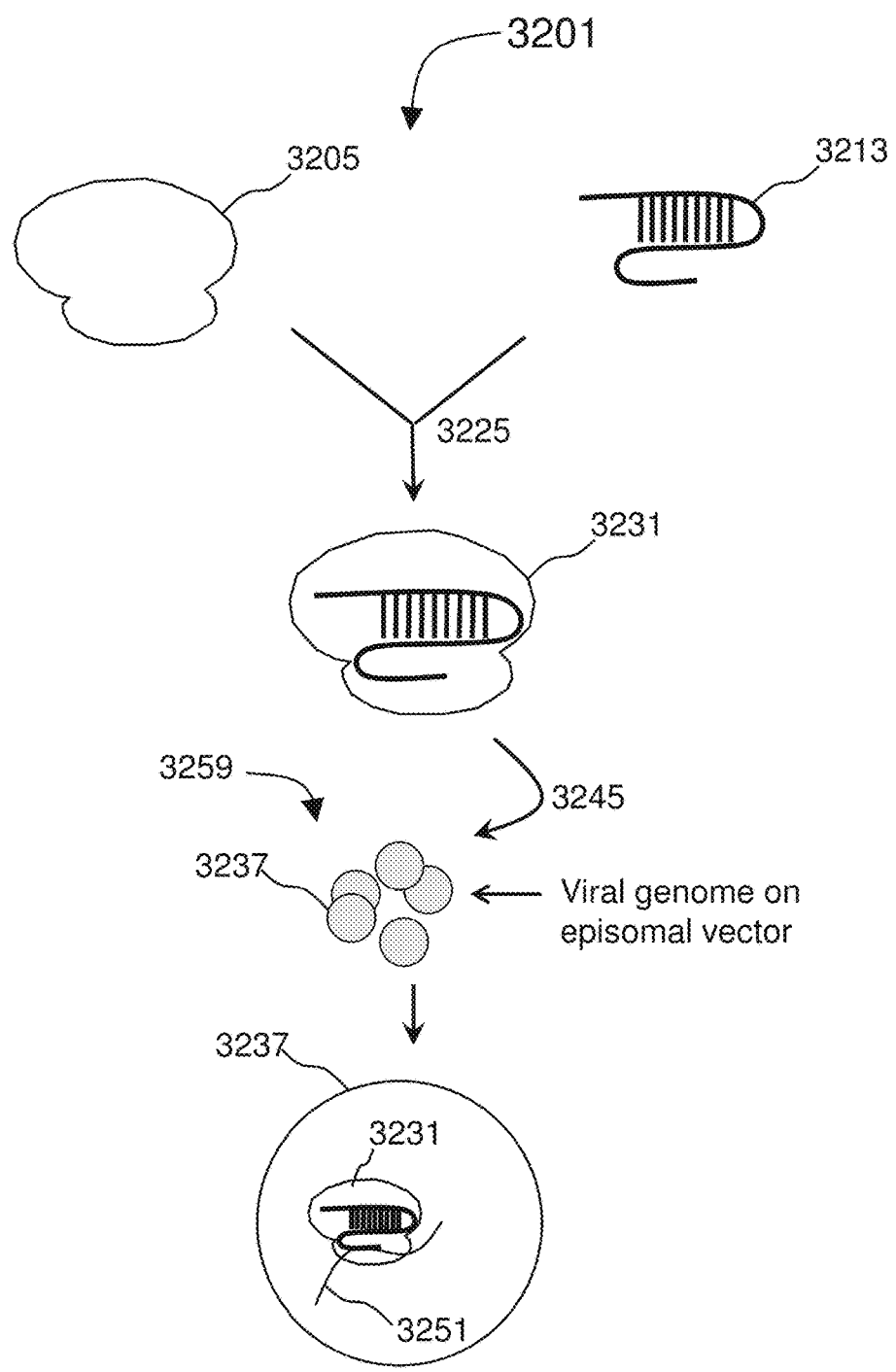
FIG. 42 shows a method 3201 for treating a cell 3237 to remove foreign nucleic acid.

FIG. 42 shows a method 3201 for treating a cell 3237 to remove foreign nucleic acid such as a viral nucleic acid 3251 from a herpes simplex virus. The method 3201 may be used to treat an infection, or the method 3201 may be used in vitro in research and development to remove foreign nucleic acid from subject cells such as cells from a human.

The method 3201 includes the steps of: forming 3225 a ribonucleoprotein (RNP) 3231 that includes a nuclease 3205 and an RNA 3213; obtaining a cell 3237 from a donor; delivering 3245 (preferably in vitro) the RNP 3231 to the cell 3237; and cleaving viral nucleic acid 3251 within the cell 3237 with the RNP 3231. The method 3201 may include providing the cell 3237 for transplantation into a patient.

The delivering 3245 may include electroporation, or the RNP may be packaged in a liposome for the delivering 3245. In some embodiments, the viral nucleic acid 3251 will exist as an episomal viral genome, i.e., an episome or episomal vector, of a virus. The RNA 3213 has a portion that is substantially complementary to a target within a viral nucleic acid 3251 and preferably not substantially complementary to any location on a human genome. In the preferred embodiments, the virus is a herpes family virus such as one selected from the group consisting of HSV-1, HSV-2, Varicella zoster virus, Epstein-Barr virus, and Cytomegalovirus. The virus may be in a latent stage in the cell.

In a preferred embodiment, the nuclease 3205 is a Crisper-associated protein such as, preferably, Cas9. The RNA 3213 may be a single guide RNA (sgRNA) (providing the functionality of crRNA and tracrRNA). In the preferred embodiment, the nuclease 3205 and the RNA 3213 are delivered to the cell as the RNP 3231.

In preferred embodiments, the cell 3237 has the viral nucleic acid 3251 therein, and the method further comprises cleaving the viral nucleic acid using the nuclease.

In some embodiments, it may be found that RNP is preferable (e.g., to plasmid DNA) for clinical applications, particularly for parenteral delivery. RNP is the active preformed drug which offers advantages to DNA (AAV) or mRNA. No need to transcribe, translate, or assemble drug components within cell. Delivery of RNP 3231 may offer improved drug properties, e.g. earlier onset activity and controlled clearance (toxicity).

Figure 36:
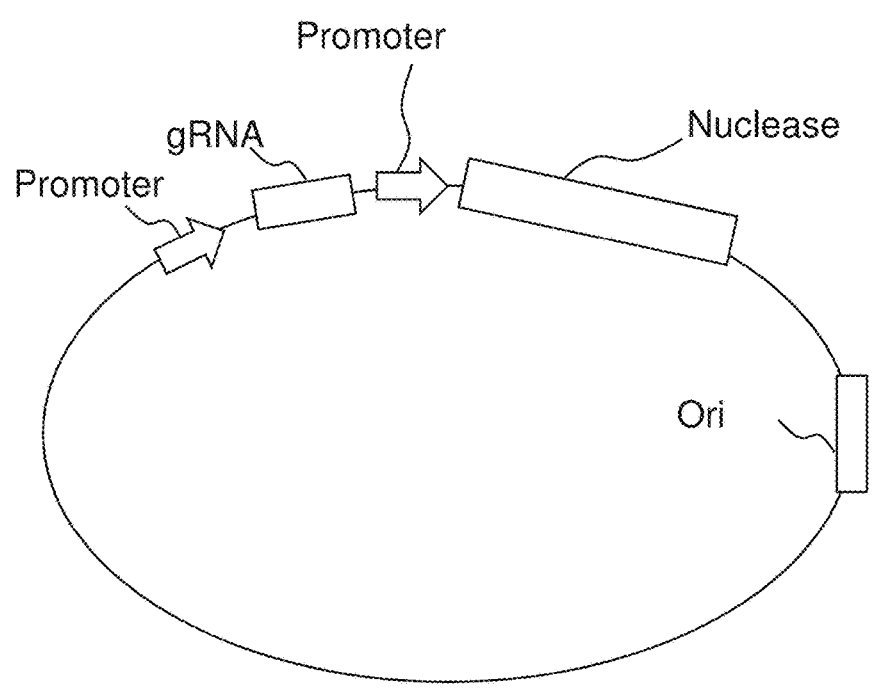
FIG. 36 shows a composition for treating a viral infection.

FIG. 36 shows a composition for treating a viral infection according to certain embodiments. The composition preferably includes a vector (which may be a plasmid, linear DNA, or a viral vector) that codes for a nuclease and a targeting moiety (e.g., a gRNA) that targets the nuclease to HSV and may be complimentary to a genomic region of HSV such as RL2, LAT, UL9, or OriS. The composition may optionally include one or more of a promoter, replication origin, other elements, or combinations thereof as described further herein.

ii. Nuclease

Methods of the invention include using a programmable or targetable nuclease to specifically target viral nucleic acid for destruction. Any suitable targeting nuclease can be used including, for example, zinc-finger nucleases (ZFNs), transcription activator-like effector nucleases (TALENs), clustered regularly interspaced short palindromic repeat (CRISPR) nucleases, meganucleases, other endo- or exo-nucleases, or combinations thereof. See Schiffer, 2012, Targeted DNA mutagenesis for the cure of chronic viral infections, J Virol 88(17):8920-8936, incorporated by reference.

CRISPR methodologies employ a nuclease, CRISPR-associated (Cas9), that complexes with small RNAs as guides (gRNAs) to cleave DNA in a sequence-specific manner upstream of the protospacer adjacent motif (PAM) in any genomic location. CRISPR may use separate guide RNAs known as the crRNA and tracrRNA. These two separate RNAs have been combined into a single RNA to enable site-specific mammalian genome cutting through the design of a short guide RNA. Cas9 and guide RNA (gRNA) may be synthesized by known methods. Cas9/guide-RNA (gRNA) uses a non-specific DNA cleavage protein Cas9, and an RNA oligo to hybridize to target and recruit the Cas9/gRNA complex. See Chang et al., 2013, Genome editing with RNA-guided Cas9 nuclease in zebrafish embryos, Cell Res 23:465-472; Hwang et al., 2013, Efficient genome editing in zebrafish using a CRISPR-Cas system, Nat. Biotechnol 31:227-229; Xiao et al., 2013, Chromosomal deletions and inversions mediated by TALENS and CRISPR/Cas in zebrafish, Nucl Acids Res 1-11.

CRISPR(Clustered Regularly Interspaced Short Palindromic Repeats) is found in bacteria and is believed to protect the bacteria from phage infection. It has recently been used as a means to alter gene expression in eukaryotic DNA, but has not been proposed as an anti-viral therapy or more broadly as a way to disrupt genomic material. Rather, it has been used to introduce insertions or deletions as a way of increasing or decreasing transcription in the DNA of a targeted cell or population of cells. See for example, Horvath et al., Science (2010) 327:167-170; Terns et al., Current Opinion in Microbiology (2011) 14:321-327; Bhaya et al. Annu Rev Genet (2011) 45:273-297; Wiedenheft et al. Nature (2012) 482:331-338); Jinek M et al. Science (2012) 337:816-821; Cong L et al. Science (2013) 339:819-823; Jinek M et al. (2013) eLife 2:e00471; Mali P et al. (2013) Science 339:823-826; Qi LS et al. (2013) Cell 152:1173-1183; Gilbert LA et al. (2013) Cell 154:442-451; Yang H et al. (2013) Cell 154:1370-1379; and Wang H et al. (2013) Cell 153:910-918); the contents of each of which are incorporated by reference in their entirety for all purposes.

In an aspect of the invention, the Cas9 endonuclease causes a double strand break in at least two locations in the genome. These two double strand breaks cause a fragment of the genome to be deleted. Even if viral repair pathways anneal the two ends, there will still be a deletion in the genome. One or more deletions using the mechanism will incapacitate the viral genome. The result is that the host cell will be free of viral infection.

In embodiments of the invention, nucleases cleave the genome of the target virus. A nuclease is an enzyme capable of cleaving the phosphodiester bonds between the nucleotide subunits of nucleic acids. Endonucleases are enzymes that cleave the phosphodiester bond within a polynucleotide chain. Some, such as Deoxyribonuclease I, cut DNA relatively nonspecifically (without regard to sequence), while many, typically called restriction endonucleases or restriction enzymes, cleave only at very specific nucleotide sequences. In a preferred embodiment of the invention, the Cas9 nuclease is incorporated into the compositions and methods of the invention, however, it should be appreciated that any nuclease may be utilized.

In preferred embodiments of the invention, the Cas9 nuclease is used to cleave the genome. The Cas9 nuclease is capable of creating a double strand break in the genome. The Cas9 nuclease has two functional domains: RuvC and HNH, each cutting a different strand. When both of these domains are active, the Cas9 causes double strand breaks in the genome.

In some embodiments of the invention, insertions into the genome can be designed to cause incapacitation, or altered genomic expression. Additionally, insertions/deletions are also used to introduce a premature stop codon either by creating one at the double strand break or by shifting the reading frame to create one downstream of the double strand break. Any of these outcomes of the NHEJ repair pathway can be leveraged to disrupt the target gene. The changes introduced by the use of the CRISPR/gRNA/Cas9 system are permanent to the genome.

In some embodiments of the invention, at least one insertion is caused by the CRISPR/gRNA/Cas9 complex. In a preferred embodiment, numerous insertions are caused in the genome, thereby incapacitating the virus. In an aspect of the invention, the number of insertions lowers the probability that the genome may be repaired.

In some embodiments of the invention, at least one deletion is caused by the CRISPR/gRNA/Cas9 complex. In a preferred embodiment, numerous deletions are caused in the genome, thereby incapacitating the virus. In an aspect of the invention, the number of deletions lowers the probability that the genome may be repaired. In a highly-preferred embodiment, the CRISPR/Cas9/gRNA system of the invention causes significant genomic disruption, resulting in effective destruction of the viral genome, while leaving the host genome intact.

TALENs uses a nonspecific DNA-cleaving nuclease fused to a DNA-binding domain that can be to target essentially any sequence. For TALEN technology, target sites are identified and expression vectors are made. Linearized expression vectors (e.g., by NotI) may be used as template for mRNA synthesis. A commercially available kit may be use such as the mMESSAGE mMACHINE SP6 transcription kit from Life Technologies (Carlsbad, Calif.). See Joung & Sander, 2013, TALENs: a widely applicable technology for targeted genome editing, Nat Rev Mol Cell Bio 14:49-55.

TALENs and CRISPR methods provide one-to-one relationship to the target sites, i.e. one unit of the tandem repeat in the TALE domain recognizes one nucleotide in the target site, and the crRNA, gRNA, or sgRNA of CRISPR/Cas system hybridizes to the complementary sequence in the DNA target. Methods can include using a pair of TALENs or a Cas9 protein with one gRNA to generate double-strand breaks in the target. The breaks are then repaired via non-homologous end-joining or homologous recombination (HR).

Figure 35:
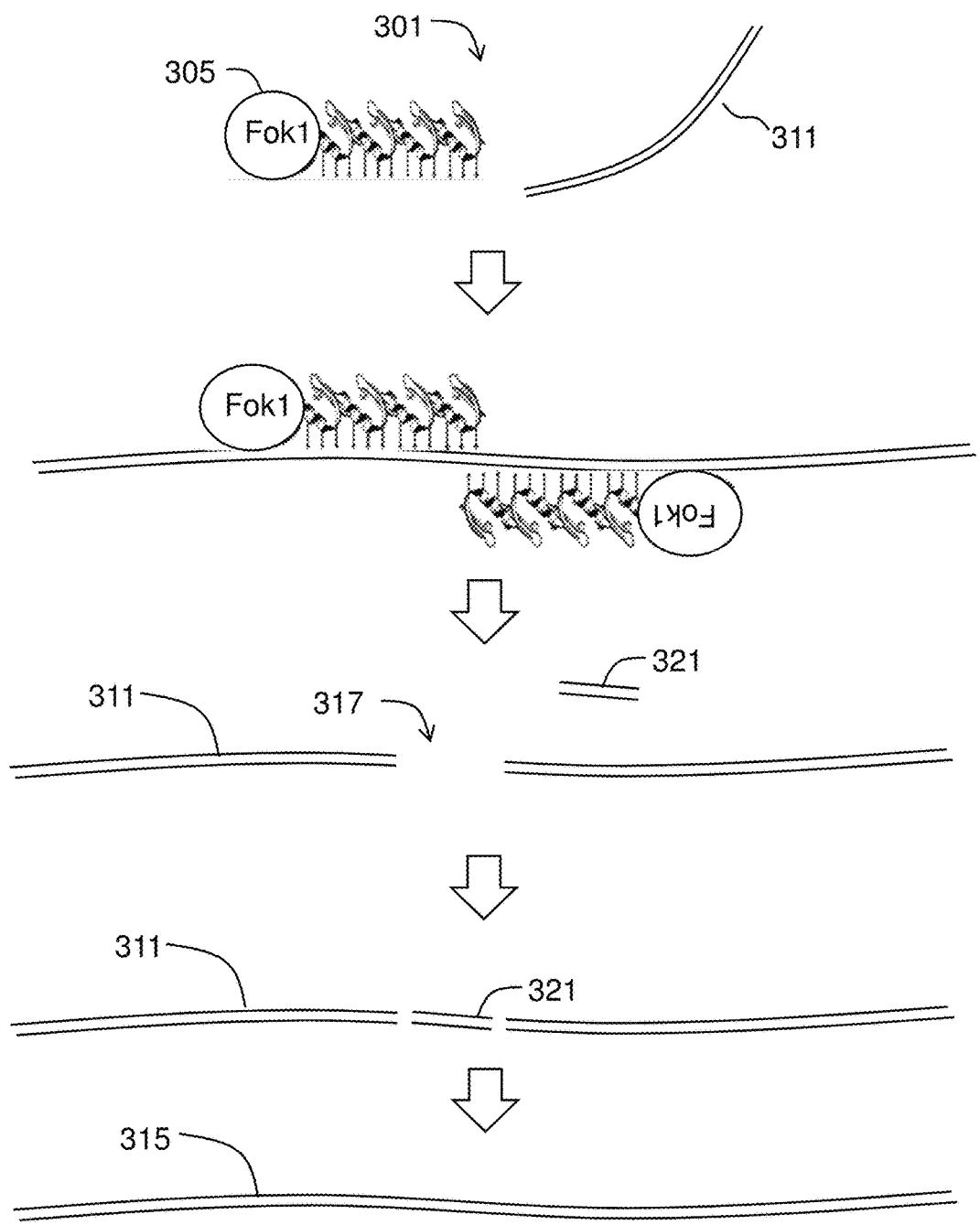
FIG. 35 shows ZFN being used to cut viral nucleic acid.

FIG. 35 shows ZFN being used to cut viral nucleic acid. Briefly, the ZFN method includes introducing into the infected host cell at least one vector (e.g., RNA molecule) encoding a targeted ZFN 305 and, optionally, at least one accessory polynucleotide. See, e.g., U.S. Pub. 2011/0023144 to Weinstein, incorporated by reference The cell includes target sequence 311. The cell is incubated to allow expression of the ZFN 305, wherein a double-stranded break 317 is introduced into the targeted chromosomal sequence 311 by the ZFN 305. In some embodiments, a donor polynucleotide or exchange polynucleotide 321 is introduced. Swapping a portion of the viral nucleic acid with irrelevant sequence can fully interfere transcription or replication of the viral nucleic acid. Target DNA 311 along with exchange polynucleotide 321 may be repaired by an error-prone non-homologous end-joining DNA repair process or a homology-directed DNA repair process.

Typically, a ZFN comprises a DNA binding domain (i.e., zinc finger) and a cleavage domain (i.e., nuclease) and this gene may be introduced as mRNA (e.g., 5' capped, polyadenylated, or both). Zinc finger binding domains may be engineered to recognize and bind to any nucleic acid sequence of choice. See, e.g., Qu et al., 2013, Zinc-finger-nucleases mediate specific and efficient excision of HIV-1 proviral DAN from infected and latently infected human T cells, Nucl Ac Res 41(16):7771-7782, incorporated by reference. An engineered zinc finger binding domain may have a novel binding specificity compared to a naturally-occurring zinc finger protein. Engineering methods include, but are not limited to, rational design and various types of selection. A zinc finger binding domain may be designed to recognize a target DNA sequence via zinc finger recognition regions (i.e., zinc fingers). See for example, U.S. Pat. Nos. 6,607,882; 6,534,261 and 6,453,242, incorporated by reference. Exemplary methods of selecting a zinc finger recognition region may include phage display and two-hybrid systems, and are disclosed in U.S. Pat. Nos. 5,789,538; 5,925,523; 6,007,988; 6,013,453; 6,410,248; 6,140,466; 6,200,759; and 6,242,568, each of which is incorporated by reference.

A ZFN also includes a cleavage domain. The cleavage domain portion of the ZFNs may be obtained from any suitable endonuclease or exonuclease such as restriction endonucleases and homing endonucleases. See, for example, Belfort & Roberts, 1997, Homing endonucleases: keeping the house in order, Nucleic Acids Res 25(17):3379-3388. A cleavage domain may be derived from an enzyme that requires dimerization for cleavage activity. Two ZFNs may be required for cleavage, as each nuclease comprises a monomer of the active enzyme dimer. Alternatively, a single ZFN may comprise both monomers to create an active enzyme dimer. Restriction endonucleases present may be capable of sequence-specific binding and cleavage of DNA at or near the site of binding. Certain restriction enzymes (e.g., Type IIS) cleave DNA at sites removed from the recognition site and have separable binding and cleavage domains. For example, the Type IIS enzyme FokI, active as a dimer, catalyzes double-stranded cleavage of DNA, at 9 nucleotides from its recognition site on one strand and 13 nucleotides from its recognition site on the other. The FokI enzyme used in a ZFN may be considered a cleavage monomer. Thus, for targeted double-stranded cleavage using a FokI cleavage domain, two ZFNs, each comprising a FokI cleavage monomer, may be used to reconstitute an active enzyme dimer. See Wah, et al., 1998, Structure of FokI has implications for DNA cleavage, PNAS 95:10564-10569; U.S. Pat. Nos. 5,356,802; 5,436,150; 5,487,994; U.S. Pub. 2005/0064474; U.S. Pub. 2006/0188987; and U.S. Pub. 2008/0131962, each incorporated by reference.

Virus targeting using ZFN may include introducing at least one donor polynucleotide comprising a sequence into the cell. A donor polynucleotide preferably includes the sequence to be introduced flanked by an upstream and downstream sequence that share sequence similarity with either side of the site of integration in the chromosome. The upstream and downstream sequences in the donor polynucleotide are selected to promote recombination between the chromosomal sequence of interest and the donor polynucleotide. Typically, the donor polynucleotide will be DNA. The donor polynucleotide may be a DNA plasmid, a bacterial artificial chromosome (BAC), a yeast artificial chromosome (YAC), a viral vector, a linear piece of DNA, a PCR fragment, a naked nucleic acid, and may employ a delivery vehicle such as a liposome. The sequence of the donor polynucleotide may include exons, introns, regulatory sequences, or combinations thereof. The double stranded break is repaired via homologous recombination with the donor polynucleotide such that the desired sequence is integrated into the chromosome. In the ZFN-mediated process, a double stranded break introduced into the target sequence by the ZFN is repaired, via homologous recombination with the exchange polynucleotide, such that the sequence in the exchange polynucleotide may be exchanged with a portion of the target sequence. The presence of the double stranded break facilitates homologous recombination and repair of the break. The exchange polynucleotide may be physically integrated or, alternatively, the exchange polynucleotide may be used as a template for repair of the break, resulting in the exchange of the sequence information in the exchange polynucleotide with the sequence information in that portion of the target sequence. Thus, a portion of the viral nucleic acid may be converted to the sequence of the exchange polynucleotide. ZFN methods can include using a vector to deliver a nucleic acid molecule encoding a ZFN and, optionally, at least one exchange polynucleotide or at least one donor polynucleotide to the infected cell.

Meganucleases are endodeoxyribonucleases characterized by a large recognition site (double-stranded DNA sequences of 12 to 40 base pairs); as a result this site generally occurs only once in any given genome. For example, the 18-base pair sequence recognized by the I-SceI meganuclease would on average require a genome twenty times the size of the human genome to be found once by chance (although sequences with a single mismatch occur about three times per human-sized genome). Meganucleases are therefore considered to be the most specific naturally occurring restriction enzymes. Meganucleases can be divided into five families based on sequence and structure motifs: LAGLIDADG, GIY-YIG, HNH, His-Cys box and PD-(D/E)XK. The most well studied family is that of the LAGLIDADG proteins, which have been found in all kingdoms of life, generally encoded within introns or inteins although freestanding members also exist. The sequence motif, LAGLIDADG, represents an essential element for enzymatic activity. Some proteins contained only one such motif, while others contained two; in both cases the motifs were followed by ~75-200 amino acid residues having little to no sequence similarity with other family members. Crystal structures illustrates mode of sequence specificity and cleavage mechanism for the LAGLIDADG family: (i) specificity contacts arise from the burial of extended β-strands into the major groove of the DNA, with the DNA binding saddle having a pitch and contour mimicking the helical twist of the DNA; (ii) full hydrogen bonding potential between the protein and DNA is never fully realized; (iii) cleavage to generate the characteristic 4-nt 3'-OH overhangs occurs across the minor groove, wherein the scissile phosphate bonds are brought closer to the protein catalytic core by a distortion of the DNA in the central "4-base" region; (iv) cleavage occurs via a proposed two-metal mechanism, sometimes involving a unique "metal sharing" paradigm; (v) and finally, additional affinity and/or specificity contacts can arise from "adapted" scaffolds, in regions outside the core α/β fold. See Silva et al., 2011, Meganucleases and other tools for targeted genome engineering, Curr Gene Ther 11(1):11-27, incorporated by reference.

In some embodiments of the invention, a template sequence is inserted into the genome. In order to introduce nucleotide modifications to genomic DNA, a DNA repair template containing the desired sequence must be present during homology directed repair (HDR). The DNA template is normally transfected into the cell along with the gRNA/Cas9. The length and binding position of each homology arm is dependent on the size of the change being introduced. In the presence of a suitable template, HDR can introduce significant changes at the Cas9 induced double strand break.

Some embodiments of the invention may utilize modified version of a nuclease. Modified versions of the Cas9 enzyme containing a single inactive catalytic domain, either RuvC- or HNH-, are called 'nickases'. With only one active nuclease domain, the Cas9 nickase cuts only one strand of the target DNA, creating a single-strand break or 'nick'. Similar to the inactive dCas9 (RuvC- and HNH-), a Cas9 nickase is still able to bind DNA based on gRNA specificity, though nickases will only cut one of the DNA strands. The majority of CRISPR plasmids are derived from *S. pyogenes* and the RuvC domain can be inactivated by a D10A mutation and the HNH domain can be inactivated by an H840A mutation.

A single-strand break, or nick, is normally quickly repaired through the HDR pathway, using the intact complementary DNA strand as the template. However, two proximal, opposite strand nicks introduced by a Cas9 nickase are treated as a double strand break, in what is often referred to as a 'double nick' or 'dual nickase' CRISPR system. A double-nick induced double strain break can be repaired by either NHEJ or HDR depending on the desired effect on the gene target. At these double strain breaks, insertions and deletions are caused by the CRISPR/Cas9 complex. In an aspect of the invention, a deletion is caused by positioning two double strand breaks proximate to one another, thereby causing a fragment of the genome to be deleted.

iii. Targeting Moiety

A nuclease may use the targeting specificity of a guide RNA (gRNA). As discussed below, guide RNAs or single guide RNAs are specifically designed to target a virus genome.

A CRISPR/Cas9 gene editing complex of the invention works optimally with a guide RNA that targets the viral genome. Guide RNA (gRNA) (which includes single guide RNA (sgRNA), crisprRNA (crRNA), transactivating RNA (tracrRNA), any other targeting oligo, or any combination thereof) leads the CRISPR/Cas9 complex to the viral genome in order to cause viral genomic disruption. In an aspect of the invention, CRISPR/Cas9/gRNA complexes are designed to target specific viruses within a cell. It should be appreciated that any virus can be targeted using the composition of the invention. Identification of specific regions of the virus genome aids in development and designing of CRISPR/Cas9/gRNA complexes.

In an aspect of the invention, the CRISPR/Cas9/gRNA complexes are designed to target latent viruses within a cell. Once transfected within a cell, the CRISPR/Cas9/gRNA complexes cause repeated insertions or deletions to render the genome incapacitated, or due to number of insertions or deletions, the probability of repair is significantly reduced.

As an example, the Epstein—Barr virus (EBV), also called human herpesvirus 4 (HHV-4) is inactivated in cells by a CRISPR/Cas9/gRNA complex of the invention. EBV is a virus of the herpes family, and is one of the most common viruses in humans. The virus is approximately 122 nm to 180 nm in diameter and is composed of a double helix of DNA wrapped in a protein capsid. In this example, the Raji cell line serves as an appropriate in vitro model. The Raji cell line is the first continuous human cell line from hematopoietic origin and cell lines produce an unusual strain of Epstein-Barr virus while being one of the most extensively studied EBV models. To target the EBV genomes in the Raji cells, a CRISPR/Cas9 complex with specificity for EBV is needed. The design of EBV-targeting CRISPR/Cas9 plasmids consisting of a U6 promoter driven chimeric guide RNA (sgRNA) and a ubiquitous promoter driven Cas9 that were obtained from Addgene, Inc. Commercially available guide RNAs and Cas9 nucleases may be used with the present invention. An EGFP marker fused after the Cas9 protein allowed selection of Cas9-positive cells.

In an aspect of the invention, guide RNAs are designed, whether or not commercially purchased, to target a specific viral genome. The viral genome is identified and guide RNA to target selected portions of the viral genome are developed and incorporated into the composition of the invention. In an aspect of the invention, a reference genome of a particular strain of the virus is selected for guide RNA design.

For example, guide RNAs that target the EBV genome are a component of the system in the present example. In relation to EBV, for example, the reference genome from strain B95-8 was used as a design guide. Within a genome of interest, such as EBV, selected regions, or genes are targeted. For example, six regions can be targeted with seven guide RNA designs for different genome editing purposes.

Figure 7:
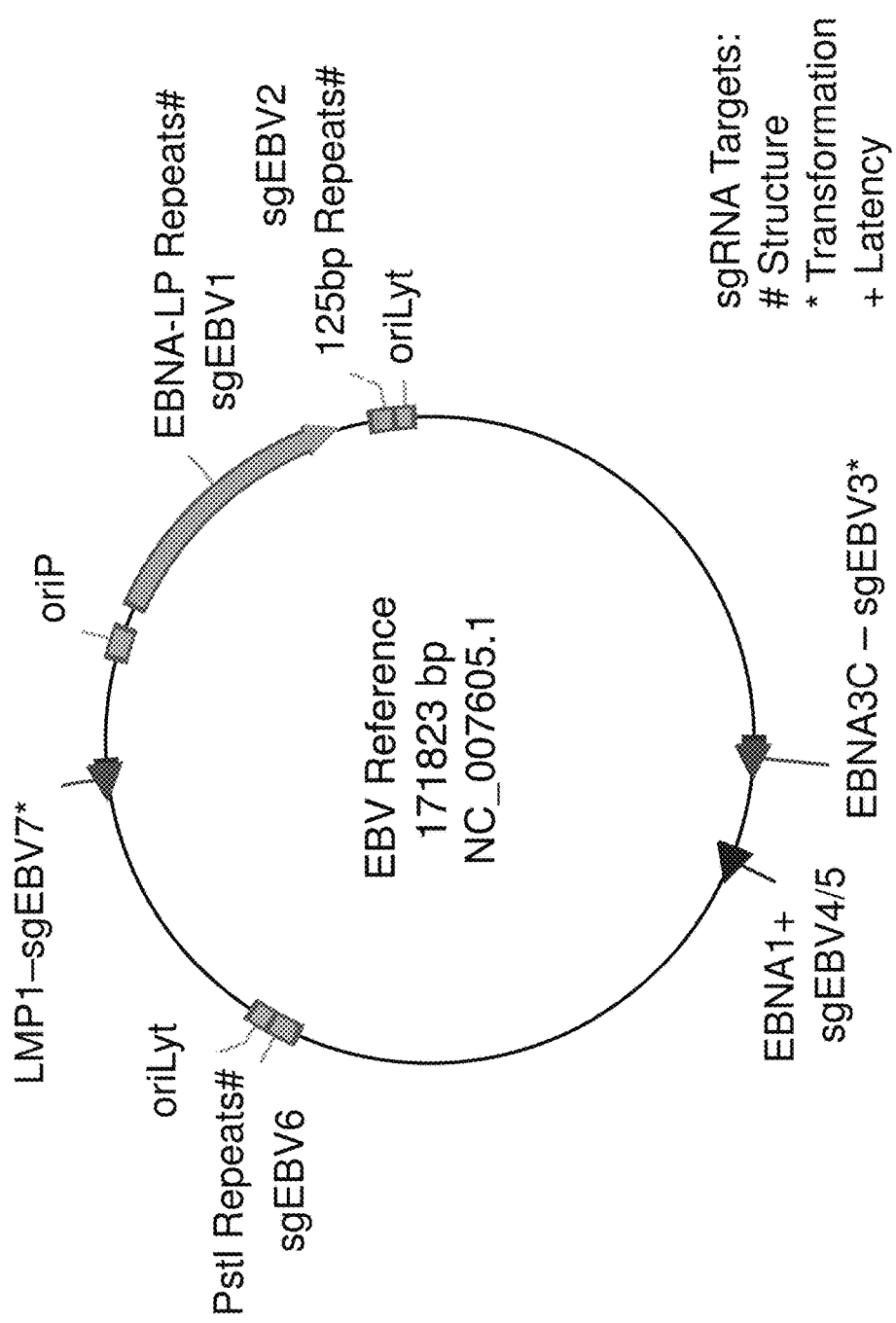
FIG. 7 is a diagram of an EBV genome, with structure-, transformation-, and latency-related targets called out.

FIG. 7 is a diagram of an EBV genome, with structure-, transformation-, and latency-related targets called out. FIG. 7 additionally shows where sgEBV1, sgEBV2, sgEBV3, sgEBV4/5, sgEBV6, and sgEBV7 target the EBV genome.

In relation to EBV, EBNA1 is the only nuclear Epstein-Barr virus (EBV) protein expressed in both latent and lytic modes of infection. While EBNA1 is known to play several important roles in latent infection, EBNA1 is crucial for many EBV functions including gene regulation and latent genome replication. Therefore, guide RNAs sgEBV4 and sgEBV5 were selected to target both ends of the EBNA1 coding region in order to excise this whole region of the genome. These "structural" targets enable systematic digestion of the EBV genome into smaller pieces. EBNA3C and LMP1 are essential for host cell transformation, and guide RNAs sgEBV3 and sgEBV7 were designed to target the 5' exons of these two proteins respectively.

iv. Introduce to Cell

Methods of the invention include introducing into a cell a nuclease and a sequence-specific targeting moiety. The nuclease is targeted to viral nucleic acid by means of the sequence-specific targeting moiety where it then cleaves the viral nucleic acid without interfering with a host genome. Any suitable method can be used to deliver the nuclease to the infected cell or tissue. For example, the nuclease or the gene encoding the nuclease may be delivered by injection, orally, or by hydrodynamic delivery. The nuclease or the gene encoding the nuclease may be delivered to systematic circulation or may be delivered or otherwise localized to a specific tissue type. The nuclease or gene encoding the nuclease may be modified or programmed to be active under only certain conditions such as by using a tissue-specific promoter so that the encoded nuclease is preferentially or only transcribed in certain tissue types.

In some embodiments, specific CRISPR/Cas9/gRNA complexes are introduced into a cell. A guide RNA is designed to target at least one category of sequences of the viral genome. In addition to latent infections this invention can also be used to control actively replicating viruses by targeting the viral genome before it is packaged or after it is ejected.

In some embodiments, a cocktail of guide RNAs may be introduced into a cell. The guide RNAs are designed to target numerous categories of sequences of the viral genome. By targeting several areas along the genome, the double strand break at multiple locations fragments the genome, lowering the possibility of repair. Even with repair mechanisms, the large deletions render the virus incapacitated.

In some embodiments, several guide RNAs are added to create a cocktail to target different categories of sequences. For example, two, five, seven or eleven guide RNAs may be present in a CRISPR cocktail targeting three different categories of sequences. However, any number of gRNAs may be introduced into a cocktail to target categories of sequences. In preferred embodiments, the categories of sequences are important for genome structure, host cell transformation, and infection latency, respectively.

In some aspects of the invention, in vitro experiments allow for the determination of the most essential targets within a viral genome. For example, to understand the most essential targets for effective incapacitation of a genome, subsets of guide RNAs are transfected into model cells. Assays can determine which guide RNAs or which cocktail is the most effective at targeting essential categories of sequences.

For example, in the case of the EBV genome targeting, seven guide RNAs in the CRISPR cocktail targeted three different categories of sequences which are identified as being important for EBV genome structure, host cell transformation, and infection latency, respectively. To understand the most essential targets for effective EBV treatment, Raji cells were transfected with subsets of guide RNAs.

Figure 14:
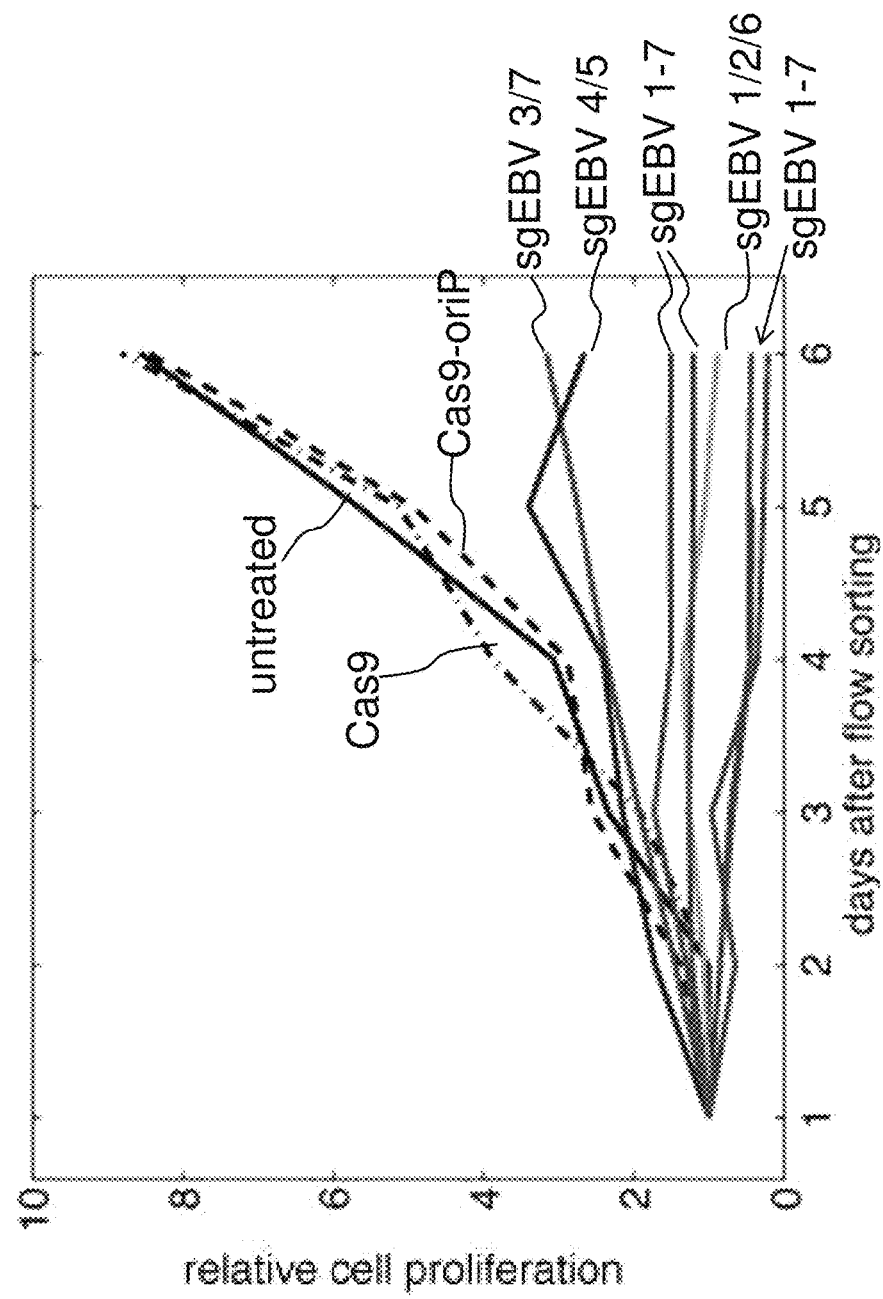
FIG. 14 shows relative cell proliferation after targeting various combinations of regions in an EBV genome with guide RNAs.

FIG. 14 shows relative cell proliferation after targeting various combinations of regions in an EBV genome with guide RNAs. Although sgEBV4/5 reduced the EBV genome by 85%, they could not suppress cell proliferation as effectively as the full cocktail (FIG. 14). Guide RNAs targeting the structural sequences (sgEBV1/2/6) could stop cell proliferation completely, despite not eliminating the full EBV load (26% decrease). Given the high efficiency of genome editing and the proliferation arrest, it was suspect that the residual EBV genome signature in sgEBV1/2/6 was not due to intact genomes but to free-floating DNA that has been digested out of the EBV genome, i.e. as a false positive.

Once CRISPR/Cas9/gRNA complexes are constructed, the complexes are introduced into a cell. It should be appreciated that complexes can be introduced into cells in an in vitro model or an in vivo model. In an aspect of the invention, CRISPR/Cas9/gRNA complexes are designed to not leave intact genomes of a virus after transfection and complexes are designed for efficient transfection.

Aspects of the invention allow for CRISPR/Cas9/gRNA to be transfected into cells by various methods, including viral vectors and non-viral vectors. Viral vectors may include retroviruses, lentiviruses, adenoviruses, and adeno-associated viruses. It should be appreciated that any viral vector may be incorporated into the present invention to effectuate delivery of the CRISPR/Cas9/gRNA complex into a cell. Some viral vectors may be more effective than others, depending on the CRISPR/Cas9/gRNA complex designed for digestion or incapacitation. In an aspect of the invention, the vectors contain essential components such as origin of replication, which is necessary for the replication and maintenance of the vector in the host cell.

In an aspect of the invention, viral vectors are used as delivery vectors to deliver the complexes into a cell. Use of viral vectors as delivery vectors are known in the art. See for example U.S. Pub. 2009/0017543 to Wilkes et al., the contents of which are incorporated by reference.

A retrovirus is a single-stranded RNA virus that stores its nucleic acid in the form of an mRNA genome (including the 5' cap and 3' PolyA tail) and targets a host cell as an obligate parasite. In some methods in the art, retroviruses have been used to introduce nucleic acids into a cell. Once inside the host cell cytoplasm the virus uses its own reverse transcriptase enzyme to produce DNA from its RNA genome, the reverse of the usual pattern, thus retro (backwards). This new DNA is then incorporated into the host cell genome by an integrase enzyme, at which point the retroviral DNA is referred to as a provirus. For example, the recombinant retroviruses such as the Moloney murine leukemia virus have the ability to integrate into the host genome in a stable fashion. They contain a reverse transcriptase that allows integration into the host genome. Retroviral vectors can either be replication-competent or replication-defective. In some embodiments of the invention, retroviruses are incorporated to effectuate transfection into a cell, however the CRISPR/Cas9/gRNA complexes are designed to target the viral genome.

In some embodiments of the invention, lentiviruses, which are a subclass of retroviruses, are used as viral vectors. Lentiviruses can be adapted as delivery vehicles (vectors) given their ability to integrate into the genome of non-dividing cells, which is the unique feature of lentiviruses as other retroviruses can infect only dividing cells. The viral genome in the form of RNA is reverse-transcribed when the virus enters the cell to produce DNA, which is then inserted into the genome at a random position by the viral integrase enzyme. The vector, now called a provirus, remains in the genome and is passed on to the progeny of the cell when it divides.

As opposed to lentiviruses, adenoviral DNA does not integrate into the genome and is not replicated during cell division. Adenovirus and the related AAV would be potential approaches as delivery vectors since they do not integrate into the host's genome. In some aspects of the invention, only the viral genome to be targeted is effected by the CRISPR/Cas9/gRNA complexes, and not the host's cells.

Adeno-associated virus (AAV) is a small virus that infects humans and some other primate species. AAV can infect both dividing and non-dividing cells and may incorporate its genome into that of the host cell. For example, because of its potential use as a gene therapy vector, researchers have created an altered AAV called self-complementary adeno-associated virus (scAAV). Whereas AAV packages a single strand of DNA and requires the process of second-strand synthesis, scAAV packages both strands which anneal together to form double stranded DNA. By skipping second strand synthesis scAAV allows for rapid expression in the cell. Otherwise, scAAV carries many characteristics of its AAV counterpart. Methods of the invention may incorporate herpesvirus, poxvirus, alphavirus, or vaccinia virus as a means of delivery vectors.

In certain embodiments of the invention, non-viral vectors may be used to effectuate transfection. Methods of non-viral delivery of nucleic acids include lipofection, nucleofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355, the contents of each of which are incorporated by reference in their entirety for all purposes.) and lipofection reagents are sold commercially (e.g., Transfectam and Lipofectin). Cationic and neutral lipids that are suitable for efficient receptor-recognition lipofection of polynucleotides include those described in U.S. Pat. No. 7,166,298 to Jessee or U.S. Pat. No. 6,890,554 to Jesse, the contents of each of which are incorporated by reference. Delivery can be to cells (e.g. in vitro or ex vivo administration) or target tissues (e.g. in vivo administration).

Synthetic vectors are typically based on cationic lipids or polymers which can complex with negatively charged nucleic acids to form particles with a diameter in the order of 100 nm. The complex protects nucleic acid from degradation by nuclease. Moreover, cellular and local delivery strategies have to deal with the need for internalization, release, and distribution in the proper subcellular compartment. Systemic delivery strategies encounter additional hurdles, for example, strong interaction of cationic delivery vehicles with blood components, uptake by the reticuloendothelial system, kidney filtration, toxicity and targeting ability of the carriers to the cells of interest. Modifying the surfaces of the cationic non-virals can minimize their interaction with blood components, reduce reticuloendothelial system uptake, decrease their toxicity and increase their binding affinity with the target cells. Binding of plasma proteins (also termed opsonization) is the primary mechanism for RES to recognize the circulating nanoparticles. For example, macrophages, such as the Kupffer cells in the liver, recognize the opsonized nanoparticles via the scavenger receptor.

In some embodiments of the invention, non-viral vectors are modified to effectuate targeted delivery and transfection. PEGylation (i.e. modifying the surface with polyethyleneglycol) is the predominant method used to reduce the opsonization and aggregation of non-viral vectors and minimize the clearance by reticuloendothelial system, leading to a prolonged circulation lifetime after intravenous (i.v.) administration. PEGylated nanoparticles are therefore often referred as "stealth" nanoparticles. The nanoparticles that are not rapidly cleared from the circulation will have a chance to encounter infected cells.

However, PEG on the surface can decrease the uptake by target cells and reduce the biological activity. Therefore, to attach targeting ligand to the distal end of the PEGylated component is necessary; the ligand is projected beyond the PEG "shield" to allow binding to receptors on the target cell surface. When cationic liposome is used as gene carrier, the application of neutral helper lipid is helpful for the release of nucleic acid, besides promoting hexagonal phase formation to enable endosomal escape. In some embodiments of the invention, neutral or anionic liposomes are developed for systemic delivery of nucleic acids and obtaining therapeutic effect in experimental animal model. Designing and synthesizing novel cationic lipids and polymers, and covalently or noncovalently binding gene with peptides, targeting ligands, polymers, or environmentally sensitive moieties also attract many attentions for resolving the problems encountered by non-viral vectors. The application of inorganic nanoparticles (for example, metallic nanoparticles, iron oxide, calcium phosphate, magnesium phosphate, manganese phosphate, double hydroxides, carbon nanotubes, and quantum dots) in delivery vectors can be prepared and surface-functionalized in many different ways.

Guided nuclease systems of the invention may be administered alone or as an active ingredient in combination with pharmaceutically acceptable carriers, diluents, adjuvants and vehicles. Vectors may be incorporated into topical or intravenous formulations which may comprise a liquid or solid filler, diluent, excipient, solvent or encapsulating material, involved in carrying or transporting the subject agents from one organ, or portion of the body, to another organ, or portion of the body. Each carrier should be compatible with the other ingredients of the formulation.

In certain embodiments, compositions of the invention may be encapsulated in hydrogels. In another embodiment, composition as disclosed herein can comprise lipid-based formulations. Any of the known lipid-based drug delivery systems can be used in the practice of the invention. For instance, multivesicular liposomes, multilamellar liposomes and unilamellar liposomes can all be used so long as a sustained release rate of the encapsulated active compound can be established. Such formulations may be used to modify the release profile of the guided nuclease compositions. Methods of making controlled release multivesicular liposome drug delivery systems are described in PCT Application Publication Nos: WO 9703652, WO 9513796, and WO 9423697, the contents of which are incorporated herein by reference.

Synthetic membrane vesicles may comprise a combination of phospholipids, usually in combination with steroids, especially cholesterol. Other phospholipids or other lipids may also be used. Examples of lipids useful in synthetic membrane vesicle production include phosphatidylglycerols, phosphatidylcholines, phosphatidylserines, phosphatidylethanolamines, sphingolipids, cerebrosides, and gangliosides, with preferable embodiments including egg phosphatidylcholine, dipalmitoylphosphatidylcholine, distearoylphosphatideholine, dioleoylphosphatidylcholine, dipalmitoylphosphatidylglycerol, and dioleoylphosphatidylglycerol.

In preparing lipid-based vesicles containing compositions of the invention, such variables as the efficiency of compound encapsulation, labiality of the compound, homogeneity and size of the resulting population of vesicles, active compound-to-lipid ratio, permeability, instability of the preparation, and pharmaceutical acceptability of the formulation should be considered.

In another embodiment, guided nuclease systems of the invention can be delivered in a vesicle, in particular a liposome (see Langer (1990) Science 249:1527-1533), the contents of which are incorporated by reference in their entirety for all purposes). In yet another embodiment, guided nuclease systems can be delivered in a controlled release system. In one embodiment, a pump may be used (see Langer (1990) supra). In another embodiment, polymeric materials can be used (see Howard et al. (1989) J. Neurosurg. 71:105, the contents of which are incorporated by reference in their entirety for all purposes). In another embodiment a vector of the invention can be administered so that it becomes intracellular, e.g., by use of a retroviral vector (see, for example, U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88: 1864-1868), the contents of which are incorporated by reference in their entirety for all purposes. Alternatively, a nucleic acid can be introduced intracellularly and incorporated within host cell DNA for expression, by homologous recombination.

In some embodiments of the invention, targeted controlled-release systems responding to the unique environments of tissues and external stimuli are utilized. Gold nanorods have strong absorption bands in the near-infrared region, and the absorbed light energy is then converted into heat by gold nanorods, the so-called 'photothermal effect'. Because the near-infrared light can penetrate deeply into tissues, the surface of gold nanorod could be modified with nucleic acids for controlled release. When the modified gold nanorods are irradiated by near-infrared light, nucleic acids are released due to thermo-denaturation induced by the photothermal effect. The amount of nucleic acids released is dependent upon the power and exposure time of light irradiation.

In some embodiments of the invention, liposomes are used to effectuate transfection into a cell or tissue. The pharmacology of a liposomal formulation of nucleic acid is largely determined by the extent to which the nucleic acid is encapsulated inside the liposome bilayer. Encapsulated nucleic acid is protected from nuclease degradation, while those merely associated with the surface of the liposome is not protected. Encapsulated nucleic acid shares the extended circulation lifetime and biodistribution of the intact liposome, while those that are surface associated adopt the pharmacology of naked nucleic acid once they disassociate from the liposome.

In some embodiments, the complexes of the invention are encapsulated in a liposome. Unlike small molecule drugs, nucleic acids cannot cross intact lipid bilayers, predominantly due to the large size and hydrophilic nature of the nucleic acid. Therefore, nucleic acids may be entrapped within liposomes with conventional passive loading technologies, such as ethanol drop method (as in SALP), reverse-phase evaporation method, and ethanol dilution method (as in SNALP).

In some embodiments, linear polyethylenimine (L-PEI) is used as a non-viral vector due to its versatility and comparatively high transfection efficiency. L-PEI has been used to efficiently deliver genes in vivo into a wide range of organs such as lung, brain, pancreas, retina, bladder as well as tumor. L-PEI is able to efficiently condense, stabilize and deliver nucleic acids in vitro and in vivo.

Low-intensity ultrasound in combination with microbubbles has recently acquired much attention as a safe method of gene delivery. Ultrasound shows tissue-permeabilizing effect. It is non-invasive and site-specific, and could make it possible to destroy tumor cells after systemic delivery, while leave nontargeted organs unaffected. Ultrasound-mediated microbubbles destruction has been proposed as an innovative method for noninvasive delivering of drugs and nucleic acids to different tissues. Microbubbles are used to carry a drug or gene until a specific area of interest is reached, and then ultrasound is used to burst the microbubbles, causing site-specific delivery of the bioactive materials. Furthermore, the ability of albumin-coated microbubbles to adhere to vascular regions with glycocalix damage or endothelial dysfunction is another possible mechanism to deliver drugs even in the absence of ultrasound. See Tsutsui et al., 2004, The use of microbubbles to target drug delivery, Cardiovasc Ultrasound 2:23, the contents of which are incorporated by reference. In ultrasound-triggered drug delivery, tissue-permeabilizing effect can be potentiated using ultrasound contrast agents, gas-filled microbubbles. The use of microbubbles for delivery of nucleic acids is based on the hypothesis that destruction of DNA-loaded microbubbles by a focused ultrasound beam during their microvascular transit through the target area will result in localized transduction upon disruption of the microbubble shell while sparing non-targeted areas.

Besides ultrasound-mediated delivery, magnetic targeting delivery could be used for delivery. Magnetic nanoparticles are usually entrapped in gene vectors for imaging the delivery of nucleic acid. Nucleic acid carriers can be responsive to both ultrasound and magnetic fields, i.e., magnetic and acoustically active lipospheres (MAALs). The basic premise is that therapeutic agents are attached to, or encapsulated within, a magnetic micro- or nanoparticle. These particles may have magnetic cores with a polymer or metal coating which can be functionalized, or may consist of porous polymers that contain magnetic nanoparticles precipitated within the pores. By functionalizing the polymer or metal coating it is possible to attach, for example, cytotoxic drugs for targeted chemotherapy or therapeutic DNA to correct a genetic defect. Once attached, the particle/therapeutic agent complex is injected into the bloodstream, often using a catheter to position the injection site near the target. Magnetic fields, generally from high-field, high-gradient, rare earth magnets are focused over the target site and the forces on the particles as they enter the field allow them to be captured and extravasated at the target.

Synthetic cationic polymer-based nanoparticles (~100 nm diameter) have been developed that offer enhanced transfection efficiency combined with reduced cytotoxicity, as compared to traditional liposomes. The incorporation of distinct layers composed of lipid molecules with varying physical and chemical characteristics into the polymer nanoparticle formulation resulted in improved efficiency through better fusion with cell membrane and entry into the cell, enhanced release of molecules inside the cell, and reduced intracellular degradation of nanoparticle complexes.

In some embodiments, the complexes are conjugated to nano-systems for systemic therapy, such as liposomes, albumin-based particles, PEGylated proteins, biodegradable polymer-drug composites, polymeric micelles, dendrimers, among others. See Davis et al., 2008, Nanotherapeutic particles: an emerging treatment modality for cancer, Nat Rev Drug Discov. 7(9):771-782, incorporated by reference. Long circulating macromolecular carriers such as liposomes, can exploit the enhanced permeability and retention effect for preferential extravasation from tumor vessels. In certain embodiments, the complexes of the invention are conjugated to or encapsulated into a liposome or polymerosome for delivery to a cell. For example, liposomal anthracyclines have achieved highly efficient encapsulation, and include versions with greatly prolonged circulation such as liposomal daunorubicin and pegylated liposomal doxorubicin. See Krishna et al., Carboxymethylcellulose-sodium based transdermal drug delivery system for propranolol, J Pharm Pharmacol. 1996 April; 48(4):367-70.

Liposomal delivery systems provide stable formulation, provide improved pharmacokinetics, and a degree of 'passive' or 'physiological' targeting to tissues. Encapsulation of hydrophilic and hydrophobic materials, such as potential chemotherapy agents, are known. See for example U.S. Pat. No. 5,466,468 to Schneider, which discloses parenterally administrable liposome formulation comprising synthetic lipids; U.S. Pat. No. 5,580,571, to Hostetler et al. which discloses nucleoside analogues conjugated to phospholipids; U.S. Pat. No. 5,626,869 to Nyqvist, which discloses pharmaceutical compositions wherein the pharmaceutically active compound is heparin or a fragment thereof contained in a defined lipid system comprising at least one amphiphatic and polar lipid component and at least one nonpolar lipid component.

Liposomes and polymerosomes can contain a plurality of solutions and compounds. In certain embodiments, the complexes of the invention are coupled to or encapsulated in polymersomes. As a class of artificial vesicles, polymersomes are tiny hollow spheres that enclose a solution, made using amphiphilic synthetic block copolymers to form the vesicle membrane. Common polymersomes contain an aqueous solution in their core and are useful for encapsulating and protecting sensitive molecules, such as drugs, enzymes, other proteins and peptides, and DNA and RNA fragments. The polymersome membrane provides a physical barrier that isolates the encapsulated material from external materials, such as those found in biological systems. Polymerosomes can be generated from double emulsions by known techniques, see Lorenceau et al., 2005, Generation of Polymerosomes from Double-Emulsions, Langmuir 21(20): 9183-6, incorporated by reference.

Some embodiments of the invention provide for a gene gun or a biolistic particle delivery system. A gene gun is a device for injecting cells with genetic information, where the payload may be an elemental particle of a heavy metal coated with plasmid DNA. This technique may also be referred to as bioballistics or biolistics. Gene guns have also been used to deliver DNA vaccines. The gene gun is able to transfect cells with a wide variety of organic and non-organic species, such as DNA plasmids, fluorescent proteins, dyes, etc.

Aspects of the invention provide for numerous uses of delivery vectors. Selection of the delivery vector is based upon the cell or tissue targeted and the specific makeup of the CRISPR/Cas9/gRNA. For example, in the EBV example discussed above, since lymphocytes are known for being resistant to lipofection, nucleofection (a combination of electrical parameters generated by a device called Nucleofector, with cell-type specific reagents to transfer a substrate directly into the cell nucleus and the cytoplasm) was necessitated for DNA delivery into the Raji cells. The Lonza pmax promoter drives Cas9 expression as it offered strong expression within Raji cells. At 24 hours after nucleofection, obvious EGFP signals were observed from a small proportion of cells through fluorescent microscopy.

Figure 6:
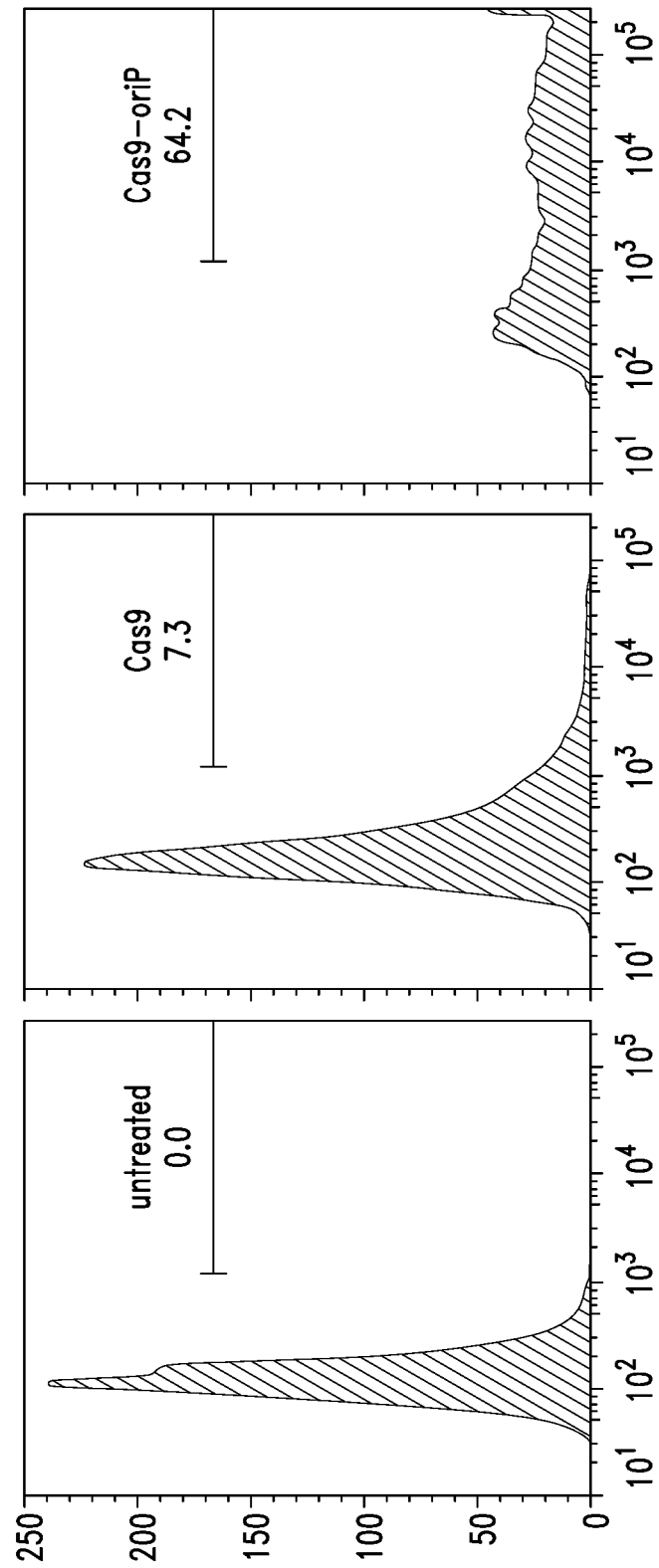
FIG. 6 shows that including an ori-P in the plasmid promoted active plasmid replication inside the cells, which increased the transfection efficiency to >60%.

FIG. 6 shows that including an ori-P in the plasmid promoted active plasmid replication inside the cells, which increased the transfection efficiency to >60%. The left panel shows that untreated cells and cells treated with a Cas9 exhibited similarly low number of cells with fluorescent markers. The right panels shows that the oriP promoted higher transfection.

The EGFP-positive cell population decreased dramatically, however, <10% transfection efficiency 48 hours after nucleofection was measured (FIG. 6). A CRISPR plasmid that included the EBV origin of replication sequence, oriP yielded a transfection efficiency >60% (FIG. 6).

Aspects of the invention utilize the CRISPR/Cas9/gRNA complexes for the targeted delivery. Common known pathways include transdermal, transmucal, nasal, ocular and pulmonary routes. Drug delivery systems may include liposomes, proliposomes, microspheres, gels, prodrugs, cyclodextrins, etc. Aspects of the invention utilize nanoparticles composed of biodegradable polymers to be transferred into an aerosol for targeting of specific sites or cell populations in the lung, providing for the release of the drug in a predetermined manner and degradation within an acceptable period of time. Controlled-release technology (CRT), such as transdermal and transmucosal controlled-release delivery systems, nasal and buccal aerosol sprays, drug-impregnated lozenges, encapsulated cells, oral soft gels, iontophoretic devices to administer drugs through skin, and a variety of programmable, implanted drug-delivery devices are used in conjunction with the complexes of the invention of accomplishing targeted and controlled delivery.

It should be appreciated that the CMV targeting nuclease can be delivered into a cell, organ, patient, or fetus by the techniques described herein and by techniques known in the art. The CMV targeting nucleases of the invention may be prepared for delivery by association (binding, encapsulating, etc.) with vectors and/or guided RNAs.

Aspects of the invention provide for delivering the CMV targeting nuclease across the placenta, or trans placental. As the conduit to the fetus, the placenta is both a drug target and a drug barrier. Alternatively, the nuclease can be introduced into the amniotic sac or into the fetus. For example, the nuclease can be introduced into the amniotic sac or into the fetus by injection. Alternatively, the fetus may be treated for CMV infection using the methods of the invention after birth, using any known technique in the art for delivering a therapeutic to an infant.

v. Cut Viral Nucleic Acid

Once inside the cell, the CRISPR/Cas9/gRNA complexes target the viral genome. In an aspect of the invention, the complexes are targeted to viral genomes. In addition to latent infections this invention can also be used to control actively replicating viruses by targeting the viral genome before it is packaged or after it is ejected. In some embodiments, methods and compositions of the invention use a nuclease such as Cas9 to target latent viral genomes, thereby reducing the chances of proliferation. The nuclease may form a complex with a gRNA (e.g., crRNA+tracrRNA or sgRNA). The complex cuts the viral nucleic acid in a targeted fashion to incapacitate the viral genome. As discussed above, the Cas9 endonuclease causes a double strand break in the viral genome. By targeted several locations along the viral genome and causing not a single strand break, but a double strand break, the genome is effectively cut a several locations along the genome. In a preferred embodiment, the double strand breaks are designed so that small deletions are caused, or small fragments are removed from the genome so that even if natural repair mechanisms join the genome together, the genome is render incapacitated.

After introduction into a cell, the CRISPR/Cas9/gRNA complexes act on the viral genome, genes, transcripts, or other viral nucleic acid. The double-strand DNA breaks generated by CRISPR are repaired with small deletions. These deletions will disrupt the protein coding and hence create knockout effects.

The nuclease, or a gene encoding the nuclease, may be delivered into an infected cell by transfection. For example, the infected cell can be transfected with DNA that encodes Cas9 and gRNA (on a single piece or separate pieces). The gRNAs are designed to localize the Cas9 endonuclease at one or several locations along the viral genome. The Cas9 endonuclease causes double strand breaks in the genome, causing small fragments to be deleted from the viral genome. Even with repair mechanisms, the deletions render the viral genome incapacitated.

Cells and tissues treated with a nuclease according to the methods of the invention are then provided for transplantation. In some embodiments, organs are treated with the nuclease to render the tissue CMV free, prior to transplantation.

In some embodiments of the invention, the nucleases are prepared for use in organs for transplant. Organ transplantation is the moving of an organ from one body to another or from a donor site to another location on the person's own body, to replace the recipient's damaged or absent organ. Organ can also be created or re-grown from the person's own cells (stem cells, or cells extracted from the failing organs) or from cells of another person. Organs can either be from a living or cadaveric source. Organs that can be transplanted are the heart, kidneys, liver, lungs, pancreas, intestine, and thymus. Tissues include bones, tendons (both referred to as musculoskeletal grafts), cornea, skin, heart valves, nerves and veins. Cornea and musculoskeletal grafts are commonly transplanted tissues, or organs.

vi. Host Genome

It will be appreciated that method and compositions of the invention can be used to target viral nucleic acid without interfering with host genetic material. Methods and compositions of the invention employ a targeting moiety such as a guide RNA that has a sequence that hybridizes to a target within the viral sequence. Methods and compositions of the invention may further use a targeted nuclease such as the cas9 enzyme, or a vector encoding such a nuclease, which uses the gRNA to bind exclusively to the viral genome and make double stranded cuts, thereby removing the viral sequence from the host.

Where the targeting moiety includes a guide RNA, the sequence for the gRNA, or the guide sequence, can be determined by examination of the viral sequence to find regions of about 20 nucleotides that are adjacent to a protospacer adjacent motif (PAM) and that do not also appear in the host genome adjacent to the protospacer motif. Preferably a guide sequence that satisfies certain similarity criteria (e.g., at least 60% identical with identity biased toward regions closer to the PAM) so that a gRNA/cas9 complex made according to the guide sequence will bind to and digest specified features or targets in the viral sequence without interfering with the host genome. Preferably, the guide RNA corresponds to a nucleotide string next to a protospacer adjacent motif (PAM) (e.g., NGG, where N is any nucleotide) in the viral sequence. Preferably, the host genome lacks any region that (1) matches the nucleotide string according to a predetermined similarity criteria and (2) is also adjacent to the PAM. The predetermined similarity criteria may include, for example, a requirement of at least 12 matching nucleotides within 20 nucleotides 5' to the PAM and may also include a requirement of at least 7 matching nucleotides within 10 nucleotides 5' to the PAM. An annotated viral genome (e.g., from GenBank) may be used to identify features of the viral sequence and finding the nucleotide string next to a protospacer adjacent motif (PAM) in the viral sequence within a selected feature (e.g., a viral replication origin, a terminal repeat, a replication factor binding site, a promoter, a coding sequence, or a repetitive region) of the viral sequence. The viral sequence and the annotations may be obtained from a genome database.

Where multiple candidate gRNA targets are found in the viral genome, selection of the sequence to be the template for the guide RNA may favor the candidate target closest to, or at the 5' most end of, a targeted feature as the guide sequence. The selection may preferentially favor sequences with neutral (e.g., 40% to 60%) GC content. Additional background regarding the RNA-directed targeting by endonuclease is discussed in U.S. Pub. 2015/0050699; U.S. Pub. 20140356958; U.S. Pub. 2014/0349400; U.S. Pub. 2014/0342457; U.S. Pub. 2014/0295556; and U.S. Pub. 2014/0273037, the contents of each of which are incorporated by reference for all purposes. Due to the existence of human genomes background in the infected cells, a set of steps are provided to ensure high efficiency against the viral genome and low off-target effect on the human genome. Those steps may include (1) target selection within viral genome, (2) avoiding PAM+target sequence in host genome, (3) methodologically selecting viral target that is conserved across strains, (4) selecting target with appropriate GC content, (5) control of nuclease expression in cells, (6) vector design, (7) validation assay, others and various combinations thereof. A targeting moiety (such as a guide RNA) preferably binds to targets within certain categories such as (i) latency related targets, (ii) infection and symptom related targets, and (iii) structure related targets.

A first category of targets for gRNA includes latency-related targets. The viral genome requires certain features in order to maintain the latency. These features include, but not limited to, master transcription regulators, latency-specific promoters, signaling proteins communicating with the host cells, etc. If the host cells are dividing during latency, the viral genome requires a replication system to maintain genome copy level. Viral replication origin, terminal repeats, and replication factors binding to the replication origin are great targets. Once the functions of these features are disrupted, the viruses may reactivate, which can be treated by conventional antiviral therapies.

A second category of targets for gRNA includes infection-related and symptom-related targets. Virus produces various molecules to facilitate infection. Once gained entrance to the host cells, the virus may start lytic cycle, which can cause cell death and tissue damage (HBV). In certain cases, such as HPV16, cell products (E6 and E7 proteins) can transform the host cells and cause cancers. Disrupting the key genome sequences (promoters, coding sequences, etc) producing these molecules can prevent further infection, and/or relieve symptoms, if not curing the disease.

A third category of targets for gRNA includes structure-related targets. Viral genome may contain repetitive regions to support genome integration, replication, or other functions. Targeting repetitive regions can break the viral genome into multiple pieces, which physically destroys the genome.

Where the nuclease is a cas protein, the targeting moiety is a guide RNA. Each cas protein requires a specific PAM next to the targeted sequence (not in the guide RNA). This is the same as for human genome editing. The current understanding the guide RNA/nuclease complex binds to PAM first, then searches for homology between guide RNA and target genome. Sternberg et al., 2014, DNA interrogation by the CRISPR RNA-guided endonuclease Cas9, Nature 507(7490):62-67. Once recognized, the DNA is digested 3-nt upstream of PAM. These results suggest that off-target digestion requires PAM in the host DNA, as well as high affinity between guide RNA and host genome right before PAM.

It may be preferable to use a targeting moiety that targets portions of the viral genome that are highly conserved. Viral genomes are much more variable than human genomes. In order to target different strains, the guide RNA will preferably target conserved regions. As PAM is important to initial sequence recognition, it is also essential to have PAM in the conserved region.

In a preferred embodiment, methods of the invention are used to deliver a nucleic acid to cells. The nucleic acid delivered to the cells may include a gRNA having the determined guide sequence or the nucleic acid may include a vector, such as a plasmid, that encodes an enzyme that will act against the target genetic material. Expression of that enzyme allows it to degrade or otherwise interfere with the target genetic material. The enzyme may be a nuclease such as the Cas9 endonuclease and the nucleic acid may also encode one or more gRNA having the determined guide sequence.

The gRNA targets the nuclease to the target genetic material. Where the target genetic material includes the genome of a virus, gRNAs complementary to parts of that genome can guide the degradation of that genome by the nuclease, thereby preventing any further replication or even removing any intact viral genome from the cells entirely. By these means, latent viral infections can be targeted for eradication.

The host cells may grow at different rate, based on the specific cell type. High nuclease expression is necessary for fast replicating cells, whereas low expression help avoiding off-target cutting in non-infected cells. Control of nuclease expression can be achieved through several aspects. If the nuclease is expressed from a vector, having the viral replication origin in the vector can increase the vector copy number dramatically, only in the infected cells. Each promoter has different activities in different tissues. Gene transcription can be tuned by choosing different promoters. Transcript and protein stability can also be tuned by incorporating stabilizing or destabilizing (ubiquitin targeting sequence, etc) motif into the sequence.

Figure 5:
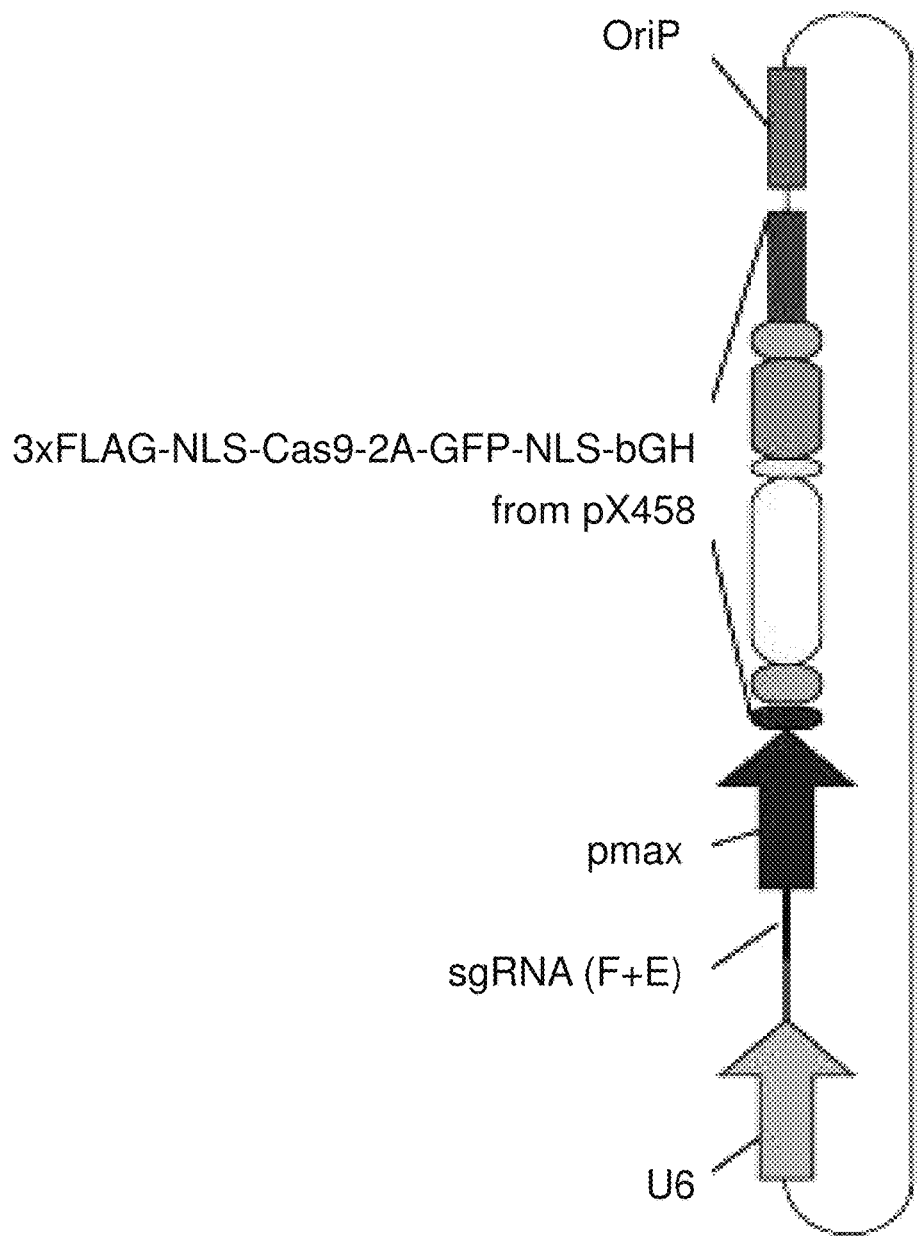
FIG. 5 shows the EGFP marker fused after the Cas9 protein, allowing selection of Cas9-positive cells.

Specific promoters may be used for the gRNA sequence, the nuclease (e.g., cas9), other elements, or combinations thereof. For example, in some embodiments, the gRNA is driven by a U6 promoter. A vector may be designed that includes a promoter for protein expression (e.g., using a promoter as described in the vector sold under the trademark PMAXCLONING by Lonza Group Ltd (Basel, Switzerland). A vector may be a plasmid (e.g., created by synthesis instrument 255 and recombinant DNA lab equipment). In certain embodiments, the plasmid includes a U6 promoter driven gRNA or chimeric guide RNA (sgRNA) and a ubiquitous promoter-driven cas9. Optionally, the vector may include a marker such as EGFP fused after the cas9 protein to allow for later selection of cas9+ cells. It is recognized that cas9 can use a gRNA (similar to the CRISPR RNA (crRNA) of the original bacterial system) with a complementary trans-activating crRNA (tracrRNA) to target viral sequences complementary to the gRNA. It has also been shown that cas9 can be programmed with a single RNA molecule, a chimera of the gRNA and tracrRNA. The single guide RNA (sgRNA) can be encoded in a plasmid and transcription of the sgRNA can provide the programming of cas9 and the function of the tracrRNA. See Jinek, 2012, A programmable dual-RNA-guided DNA endonuclease in adaptive bacterial immunity, Science 337:816-821 and especially FIG. 5A therein for background.

Using the above principles, methods and compositions of the invention may be used to target viral nucleic acid in an infected host without adversely influencing the host genome.

For additional background see Hsu, 2013, DNA targeting specificity of RNA-guided Cas9 nucleases, Nature Biotechnology 31(9):827-832; and Jinek, 2012, A programmable dual-RNA-guided DNA endonuclease in adaptive bacterial immunity, Science 337:816-821, the contents of each of which are incorporated by reference. Since the targeted locations are selected to be within certain categories such as (i) latency related targets, (ii) infection and symptom related targets, or (iii) structure related targets, cleavage of those sequences inactivates the virus and removes it from the host. Since the targeting RNA (the gRNA or sgRNA) is designed to satisfy according to similarity criteria that matches the target in the viral genetic sequence without any off-target matching the host genome, the latent viral genetic material is removed from the host without any interference with the host genome.

ii. Apoptotic Pathway

In cases where a small number of cells are infected and it would suffice to ablate the entire cell (as well as the CMV genome), an aspect of the invention contemplates administration of a vector containing a promoter which is active in the latent viral state, wherein the promoter drives a cell-killing gene. HSV is a particularly interesting target for this approach as it has been estimated that only thousands to tens of thousands neurons are latently infected. See Hoshino et al., 2008, The number of herpes simplex virus-infected neurons and the number of viral genome copies per neuron correlate with latent viral load in ganglia, Virology 372(1): 56-63, incorporated by reference. Examples of cell-killing genes include both (1) targetable nucleases that are targeted to the cell genome; and (2) apoptosis effectors such as BAX and BAK and proteins that destroy the integrity of the cell or mitochondrial membrane, such as alpha hemolysin. (Bayles, "Bacterial programmed cell death: making sense of a paradox," Nature Reviews Microbiology 12 pp. 63-69 (2014)). Having a promoter that is only activated in latently infected cells could be used not only in this context but also be used to increase selectivity of nuclease therapy by making activity specific to infected cells; an example of such a promoter is Latency-Associated Promoter 1, or "LAP1". (Preston and Efstathiou, "Molecular Basis of HSV Latency and Reactivation", in Human Herpesviruses: Biology, Therapy and Immunoprophylaxis 2007.) In some embodiments, the invention provides methods and therapeutics that can be used to cause the death of host cells but only those cells that are infected. For example, the treatment can include delivering a gene for a protein that causes cell death, where the gene is under control of a viral regulatory element such as a promoter from the genome of the infecting virus or the gene is encoded in a vector that includes a viral origin of replication. Where the virus is present, the gene will be expressed and the gene product will cause the death of the cell. The gene can code for a protein important in apoptosis, or the gene can code for a nuclease that digests the host genome.

The apoptotic embodiments may be used to remove infected cells from within a sample that contains a mix of infected and uninfected cells. Using a targetable nuclease, a composition may be provided that includes a viral-driven promoter, a targetable nuclease, and guide RNAs that target the cellular (e.g., human) genome. In the presence of the virus, the nuclease will kill the cells. The sample will be left containing only uninfected cells.

An apoptosis protein may be used as the therapeutic. The therapeutic may be provided encoded within a vector, in which the vector also encodes a sequence that causes the therapeutic to be expressed within a cell that is infected by a virus. The sequence may be a regulatory element (e.g., a promoter and an origin of replication) from the genome of the virus. The therapeutic may provide a mechanism that selectively causes death of virus-infected cells. For example, a protein may be used that restores a deficient apoptotic pathway in the cell. The gene may be, for example, BAX, BAK, BCL-2, or alpha-hemolysin. Preferably, the therapeutic induces apoptosis in the cell that is infected by the virus and does not induce apoptosis in an uninfected cell.

In some embodiments, the invention provides a composition that includes a viral vector, plasmid, or other coding nucleic acid that encodes at least one gene that promotes apoptosis and at least one promoter associated a viral genome. Apoptosis regulator Bcl-2 is a family of proteins that govern mitochondrial outer membrane permeabilization (MOMP) and include pro-apoptotic proteins such as Bax, BAD, Bak, Bok, Bcl-rambo, Bcl-xs and BOK/Mtd.

Apoptosis regulator BAX, also known as bcl-2-like protein 4, is a protein that in humans is encoded by the BAX gene. BAX is a member of the Bcl-2 gene family. This protein forms a heterodimer with BCL2, and functions as an apoptotic activator. This protein is reported to interact with, and increase the opening of, the mitochondrial voltage-dependent anion channel (VDAC), which leads to the loss in membrane potential and the release of cytochrome c.

Bcl-2 homologous antagonist/killer is a protein that in humans is encoded by the BAK1 gene on chromosome 6. This protein localizes to mitochondria, and functions to induce apoptosis. It interacts with and accelerates the opening of the mitochondrial voltage-dependent anion channel, which leads to a loss in membrane potential and the release of cytochrome c.

Human genes encoding proteins that belong to this family include: BAK1, BAX, BCL2, BCL2A1, BCL2L1, BCL2L2, BCL2L10, BCL2L13, BCL2L14, BOK, and MCL1.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1

Targeting HSV

T7 in vitro transcription produced the complete guide RNA with scaffold. Flanking regions of the genome targets were PCR amplified from HSV2 strain G genomic DNA (from ATCC). Cas9 protein (from PNA Bio), guide RNA and target DNA were mixed and incubated for in vitro endonuclease assay.

To further test the efficiency against HSV within cells, we subcloned each HSV2 amplicon mentioned above into an expression vector. The same guide RNA sequences (RL2, LATi, LATp, UL9, OriS, and US12) were also cloned into a CRISPR plasmid, containing CMV promoter driven cas9 and U6 promoter driven sgRNA scaffold. We transfected both HSV2 amplicon clones and anti-HSV CRISPR plasmid into 293T cells with Lipofectamine 2000. 72 hours after transfection, cells were harvested for genomic DNA isolation.

FIG. 3 is a gel with lanes showing genomic DNA size bands for cells treated with the RL2, LATi, LATp, UL9, OriS, and US12 guide sequences with and without Cas9.

Figure 4:
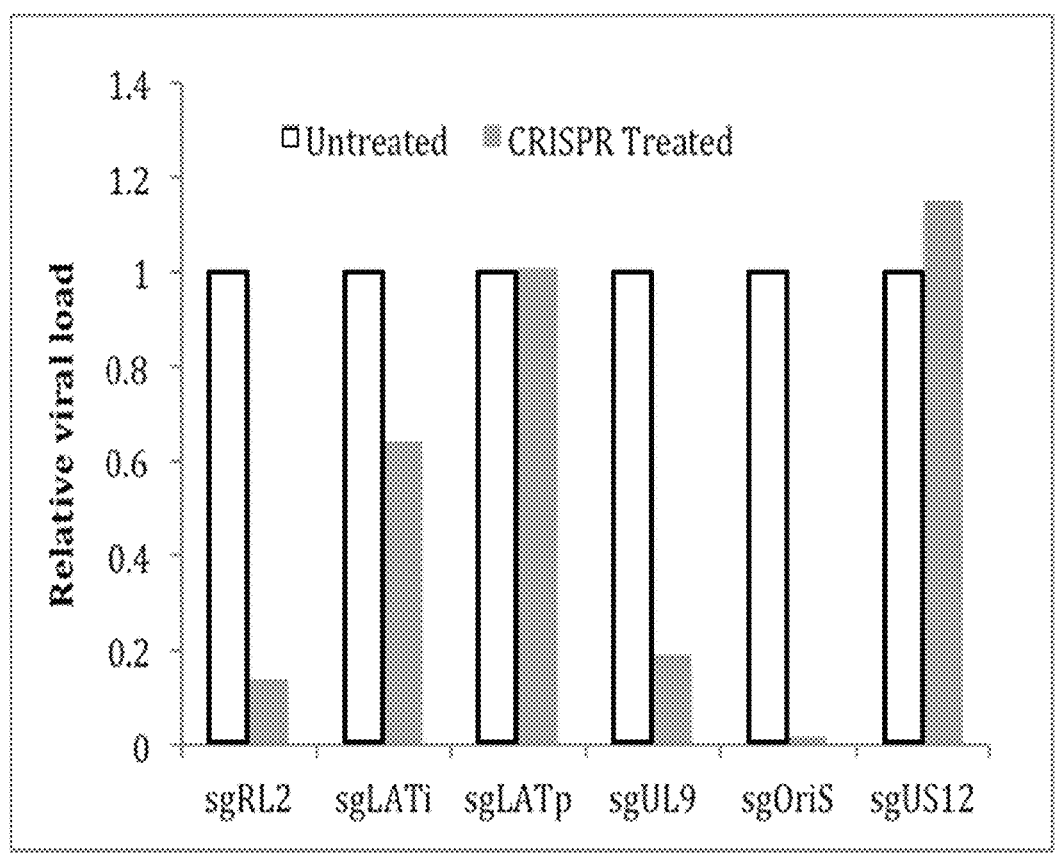
FIG. 4 shows the results of quantitative PCR assays showing different levels of decreasing of HSV DNA in the CRISPR treated samples.

FIG. 4 shows the results of quantitative PCR assays showing different levels of decreasing of HSV DNA in the CRISPR treated samples. In vivo anti-HSV treatment with a transient cell model. We used a CRISPR plasmid with a scrambled sgRNA sequence as control. DNA sample input was normalized with each control sample. OriS demonstrated the highest viral DNA elimination activity followed by RL2, UL9, and LATi.

Example 2

Targeting EBV

Burkitt's lymphoma cell lines Raji, Namalwa, and DG-75 were obtained from ATCC and cultured in RPMI 1640 supplemented with 10% FBS and PSA, following ATCC recommendation. Human primary lung fibroblast IMR-90 was obtained from Coriell and cultured in Advanced DMEM/F-12 supplemented with 10% FBS and PSA.

Plasmids consisting of a U6 promoter driven chimeric guide RNA (sgRNA) and a ubiquitous promoter driven Cas9 were obtained from addgene, as described by Cong L et al. (2013) Multiplex Genome Engineering Using CRISPR/Cas Systems. Science 339:819-823. An EGFP marker fused after the Cas9 protein allowed selection of Cas9-positive cells (FIG. 6). We adapted a modified chimeric guide RNA design for more efficient Pol-III transcription and more stable stem-loop structure (Chen B et al. (2013) Dynamic Imaging of Genomic Loci in Living Human Cells by an Optimized CRISPR/Cas System. Cell 155:1479-1491).

We obtained pX458 from Addgene, Inc. A modified CMV promoter with a synthetic intron (pmax) was PCR amplified from Lonza control plasmid pmax-GFP. A modified guide RNA sgRNA(F+E) was ordered from IDT. EBV replication origin oriP was PCR amplified from B95-8 transformed lymphoblastoid cell line GM12891. We used standard cloning protocols to clone pmax, sgRNA(F+E) and oriP to pX458, to replace the original CAG promoter, sgRNA and f1 origin. We designed EBV sgRNA based on the B95-8 reference, and ordered DNA oligos from IDT. The original sgRNA place holder in pX458 serves as the negative control.

Lymphocytes are known for being resistant to lipofection, and therefore we used nucleofection for DNA delivery into Raji cells. We chose the Lonza pmax promoter to drive Cas9 expression as it offered strong expression within Raji cells. We used the Lonza Nucleofector II for DNA delivery. 5 million Raji or DG-75 cells were transfected with 5 ug plasmids in each 100-ul reaction. Cell line Kit V and program M-013 were used following Lonza recommendation. For IMR-90, 1 million cells were transfected with 5 ug plasmids in 100 ul Solution V, with program T-030 or X-005. 24 hours after nucleofection, we observed obvious EGFP signals from a small proportion of cells through fluorescent microscopy. The EGFP-positive cell population decreased dramatically after that, however, and we measured <10% transfection efficiency 48 hours after nucleofection (FIG. 6). We attributed this transfection efficiency decrease to the plasmid dilution with cell division. To actively maintain the plasmid level within the host cells, we redesigned the CRISPR plasmid to include the EBV origin of replication sequence, oriP. With active plasmid replication inside the cells, the transfection efficiency rose to >60% (FIG. 6).

To design guide RNA targeting the EBV genome, we relied on the EBV reference genome from strain B95-8. We targeted six regions with seven guide RNA designs for different genome editing purposes.

Additional information such as primer design is shown in Wang and Quake, 2014, RNA-guided endonuclease provides a therapeutic strategy to cure latent herpesviridae infection, PNAS 111(36):13157-13162 and in the Supporting Information to that article published online at the PNAS website, and the contents of both of those documents are incorporated by reference for all purposes.

EBNA1 is crucial for many EBV functions including gene regulation and latent genome replication. Guide RNA sgEBV4 and sgEBV5 to both ends of the EBNA1 coding region in order to excise this whole region of the genome. Guide RNAs sgEBV1, 2 and 6 fall in repeat regions, so that the success rate of at least one CRISPR cut is multiplied. These "structural" targets enable systematic digestion of the EBV genome into smaller pieces. EBNA3C and LMP1 are essential for host cell transformation, and we designed guide RNAs sgEBV3 and sgEBV7 were designed to target the 5' exons of these two proteins respectively.

EBV Genome Editing. The double-strand DNA breaks generated by CRISPR are repaired with small deletions. FIGS. 8-13 represent CRISPR/Cas9 induced large deletions.

Figure 8:
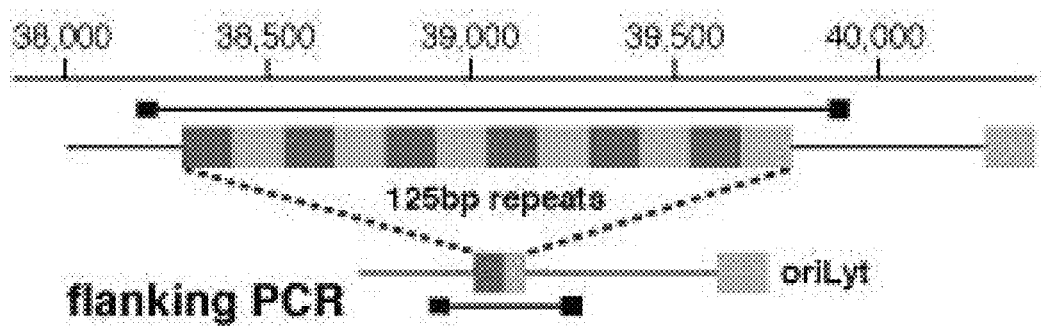
FIG. 8 shows the genome context around guide RNA sgEBV2 and PCR primer locations.

FIG. 8 shows the genome context around guide RNA sgEBV2 and PCR primer locations.

Figure 9:
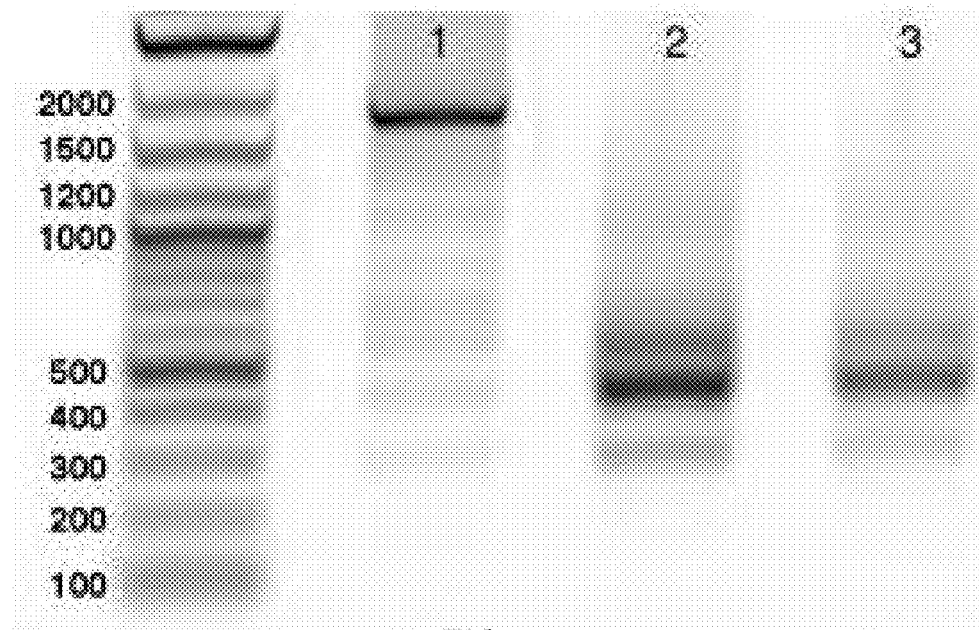
FIG. 9 shows the large deletion induced by sgEBV2 (lanes 1-3 are before, 5 days after, and 7 days after sgEBV2 treatment, respectively).

FIG. 9 shows the large deletion induced by sgEBV2. Lane 1-3 are before, 5 days after, and 7 days after sgEBV2 treatment, respectively.

Figure 10:
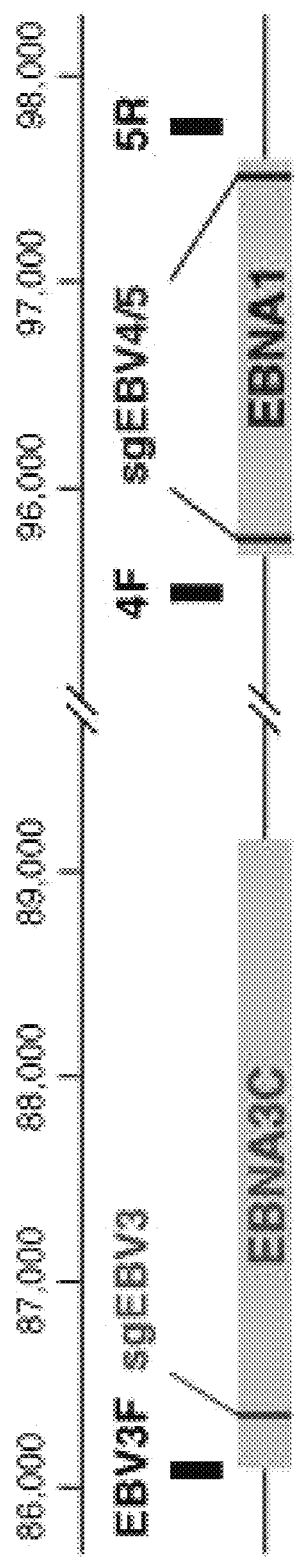
FIG. 10 shows the genome context around guide RNA sgEBV3/4/5 and PCR primer locations.

FIG. 10 shows the genome context around guide RNA sgEBV3/4/5 and PCR primer locations.

Figure 11:
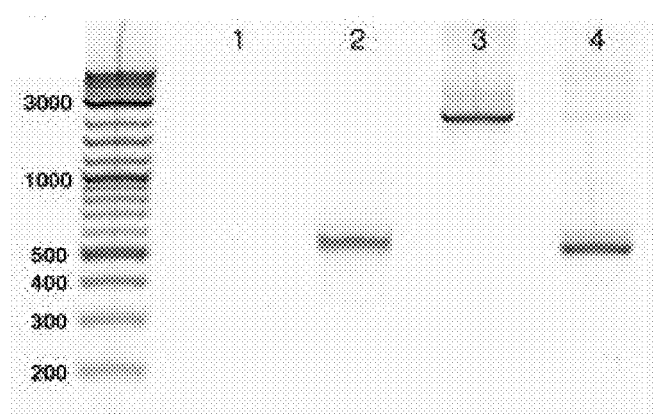
FIG. 11 shows the large deletions induced by sgEBV3/5 and sgEBV4/5. Lane 1 and 2 are 3F/5R PCR amplicons before and 8 days after sgEBV3/5 treatment. Lane 3 and 4 are 4F/5R PCR amplicons before and 8 days after sgEBV4/5 treatment.

FIG. 11 shows the large deletions induced by sgEBV3/5 and sgEBV4/5. Lane 1 and 2 are 3F/5R PCR amplicons before and 8 days after sgEBV3/5 treatment. Lane 3 and 4 are 4F/5R PCR amplicons before and 8 days after sgEBV4/5 treatment.

Figure 12:
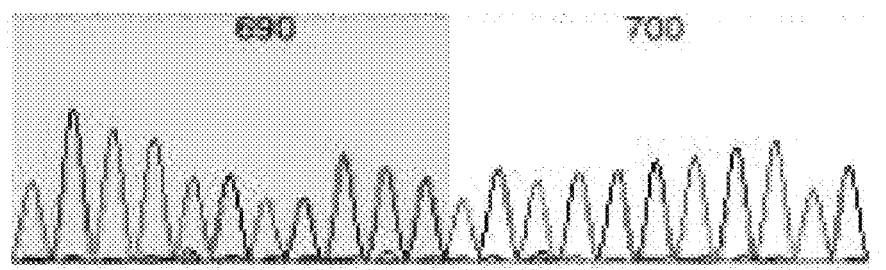
FIG. 12 shows that Sanger sequencing confirmed genome cleavage and repair ligation 8 days after sgEBV3/5.
Figure 13:
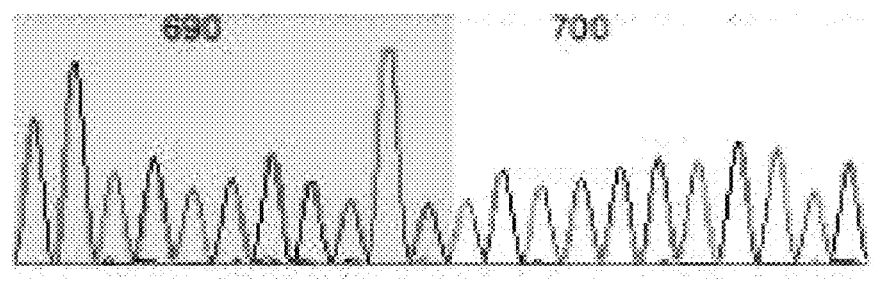
FIG. 13 shows that Sanger sequencing confirmed genome cleavage and repair ligation 8 days after sgEBV4/5.

FIGS. 12 and 13 show that Sanger sequencing confirmed genome cleavage and repair ligation 8 days after sgEBV3/5 (FIG. 12) and sgEBV4/5 (FIG. 13) treatment. Areas 690 and 700 (FIG. 12) and areas 690 and 700 (FIG. 13) indicate the two ends before repair ligation.

These deletions will disrupt the protein coding and hence create knockout effects. SURVEYOR assays confirmed efficient editing of individual sites.

Figure 32:
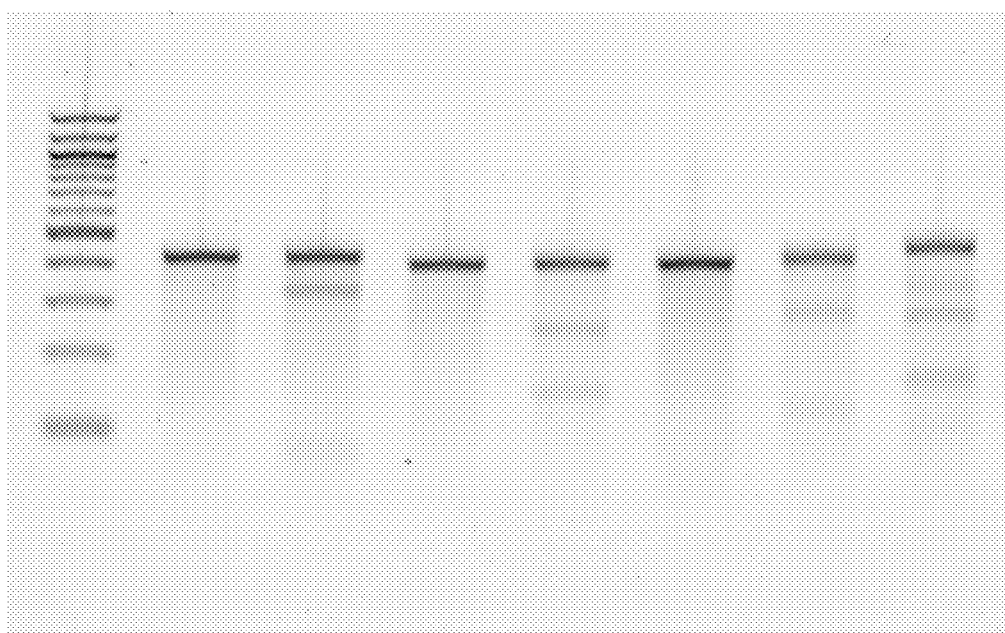
FIG. 32 represents SURVEYOR assay of EBV CRISPR (lanes numbered from left to right: Lane 1: NEB 100 bp ladder; Lane 2: sgEBV1 control; Lane 3: sgEBV1; Lane 4: sgEBV5 control; Lane 5: sgEBV5; Lane 6: sgEBV7 control; Lane 7: sgEBV7; Lane 8: sgEBV4).

FIG. 32 represents SURVEYOR assay of EBV CRISPR (lanes numbered from left to right: Lane 1: NEB 100 bp ladder; Lane 2: sgEBV1 control; Lane 3: sgEBV1; Lane 4: sgEBV5 control; Lane 5: sgEBV5; Lane 6: sgEBV7 control; Lane 7: sgEBV7; Lane 8: sgEBV4).

Beyond the independent small deletions induced by each guide RNA, large deletions between targeting sites can systematically destroy the EBV genome. Guide RNA sgEBV2 targets a region with twelve 125-bp repeat units (FIG. 8). PCR amplicon of the whole repeat region gave a ~1.8-kb band (FIG. 9). After 5 or 7 days of sgEBV2 transfection, we obtained ~0.4-kb bands from the same PCR amplification (FIG. 9). The ~1.4-kb deletion is the expected product of repair ligation between cuts in the first and the last repeat unit (FIG. 8).

DNA sequences flanking sgRNA targets were PCR amplified with Phusion DNA polymerase. SURVEYOR assays were performed following manufacturer's instruction. DNA amplicons with large deletions were TOPO cloned and single colonies were used for Sanger sequencing. EBV load was measured with Taqman digital PCR on Fluidigm BioMark. A Taqman assay targeting a conserved human locus was used for human DNA normalization. 1 ng of single-cell whole-genome amplification products from Fluidigm C1 were used for EBV quantitative PCR.

It is possible to delete regions between unique targets (FIG. 10). Six days after sgEBV4-5 transfection, PCR amplification of the whole flanking region (with primers EBV4F and 5R) returned a shorter amplicon, together with a much fainter band of the expected 2 kb (FIG. 11). Sanger sequencing of amplicon clones confirmed the direct connection of the two expected cutting sites (FIG. 13). A similar experiment with sgEBV3-5 also returned an even larger deletion, from EBNA3C to EBNA1 (FIG. 11).

Additional information such as primer design is shown in Wang and Quake, 2014, RNA-guided endonuclease provides a therapeutic strategy to cure latent herpesviridae infection, PNAS 111(36):13157-13162 and in the Supporting Information to that article published online at the PNAS website, and the contents of both of those documents are incorporated by reference for all purposes.

Figure 15:
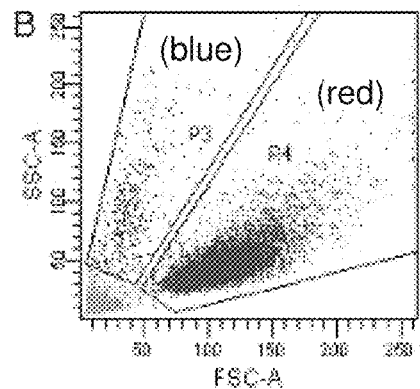
FIG. 15 gives flow cytometry scattering signals from before sgEBV1-7 treatments.
Figure 18:
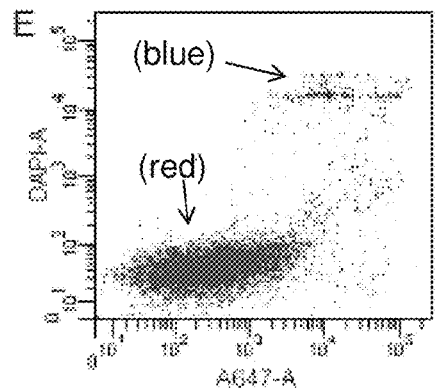
FIG. 18 shows Annexin V Alexa647 and DAPI staining results before sgEBV1-7 treatments.
Figure 16:
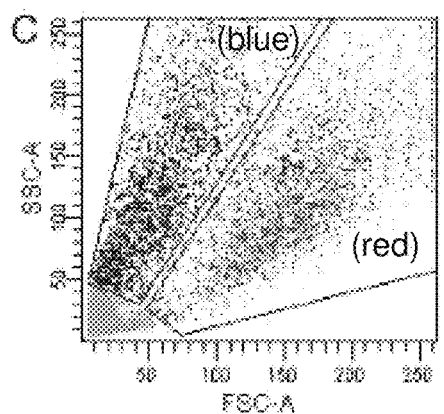
FIG. 16 gives flow cytometry scattering signals from 5 days after sgEBV1-7 treatments FIG. 17 gives flow cytometry scattering signals from 8 days after sgEBV1-7 treatments.
Figure 19:
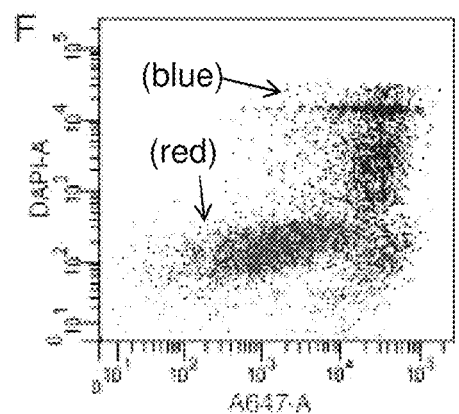
FIG. 19 shows Annexin V Alexa647 and DAPI staining results 5 days after sgEBV1-7 treatments.
Figure 17:
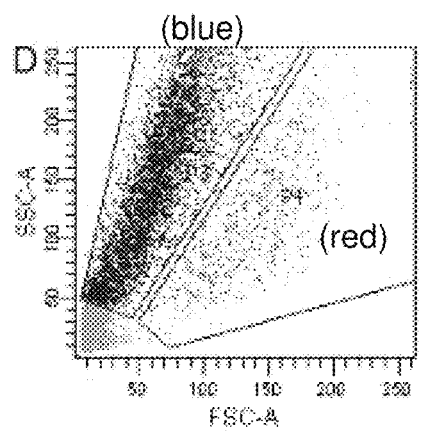
Figure 20:
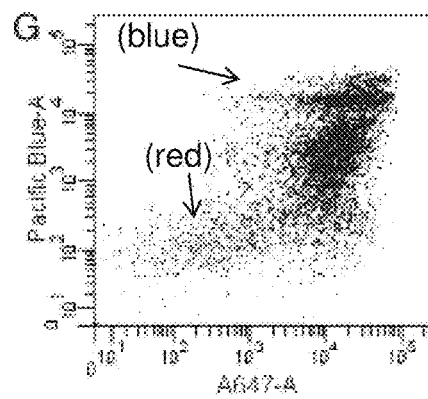
FIG. 20 shows Annexin V Alexa647 and DAPI staining results 8 days after sgEBV1-7 treatments.

Cell Proliferation Arrest With EBV Genome Destruction. Two days after CRISPR transfection, EGFP-positive cells were flow sorted for further culture and counted the live cells daily. FIGS. 14-26 represent cell proliferation arrest with EBV genome destruction. FIG. 14 shows cell proliferation curves after different CRISPR treatments. Five independent sgEBV1-7 treatments are shown here. FIGS. 15-20 show flow cytometry scattering signals before (FIG. 15), 5 days after (FIG. 16) and 8 days after (FIG. 14) sgEBV1-7 treatments. FIGS. 18-20 show Annexin V Alexa647 and DAPI staining results before (FIG. 18), 5 days after (FIG. 19) and 8 days after (FIG. 20) sgEBV1-7 treatments. Regions 300 and 200 correspond to subpopulation P3 and P4 in (FIGS. 15-17).

Figure 21:
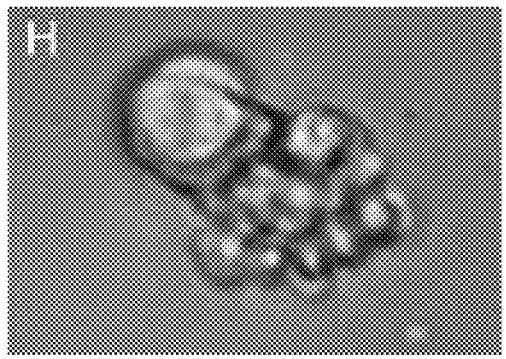
FIGS. 21 and 22 show microscopy revealed apoptotic cell morphology after sgEBV1-7 treatment.
Figure 22:
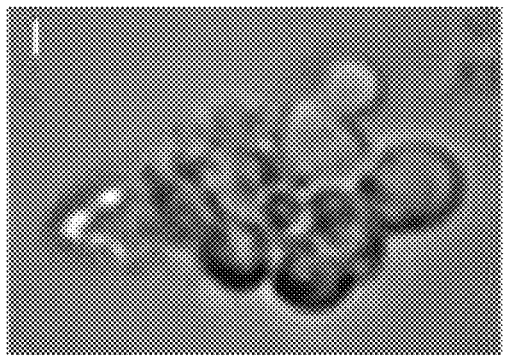

FIGS. 21 and 22 show microscopy revealed apoptotic cell morphology after sgEBV1-7 treatment.

Figure 23:
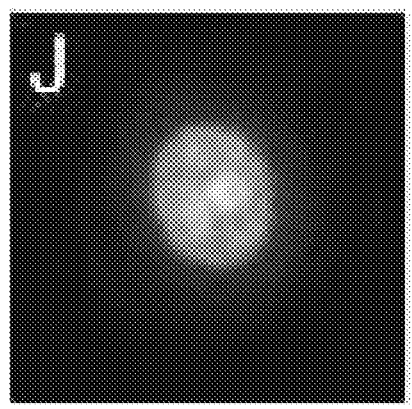
FIG. 23 shows nuclear morphology before sgEBV1-7 treatment.

FIG. 23 shows nuclear morphology before sgEBV1-7 treatment.

Figure 24:
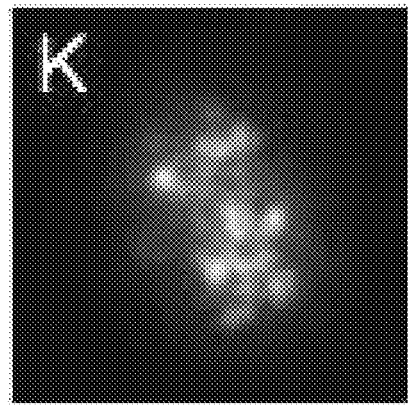
FIGS. 24-26 show nuclear morphology after sgEBV1-7 treatment.
Figure 25:
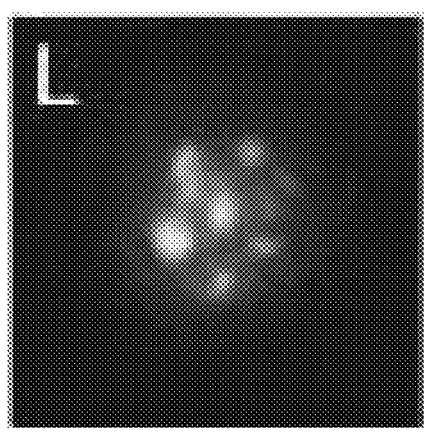
Figure 26:
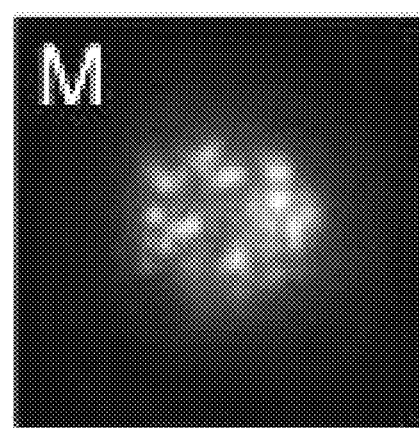

FIGS. 24-26 show nuclear morphology after sgEBV1-7 treatment.

As expected, cells treated with Cas9 plasmids which lacked oriP or sgEBV lost EGFP expression within a few days and proliferated with a rate similar rate to the untreated control group (FIG. 14). Plasmids with Cas9-oriP and a scrambled guide RNA maintained EGFP expression after 8 days, but did not reduce the cell proliferation rate. Treatment with the mixed cocktail sgEBV1-7 resulted in no measurable cell proliferation and the total cell count either remained constant or decreased (FIG. 14).

FIG. 15 shows that flow cytometry scattering signals clearly revealed alterations in the cell morphology after sgEBV1-7 treatment, as the majority of the cells shrank in size with increasing granulation (P4 to P3 shift).

FIG. 19 gives DAPI staining results showing that cells in population P3 also demonstrated compromised membrane permeability. To rule out the possibility of CRISPR cytotoxicity, especially with multiple guide RNAs, the same treatment was performed on two other samples: the EBV-negative Burkitt's lymphoma cell line DG-75 and primary human lung fibroblast IMR90.

Figure 33:
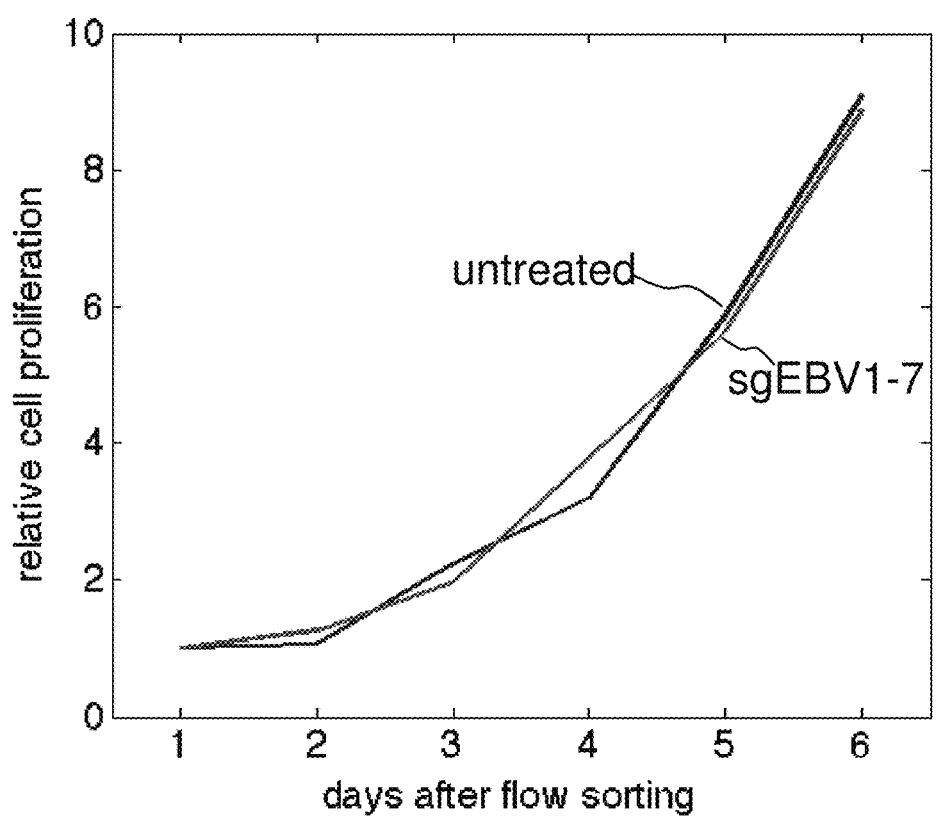
FIG. 33 shows that the CRISPR treatments were not cytotoxic to the EBV-negative Burkitt's lymphoma cell line DG-75

FIG. 33 shows that the CRISPR treatments were not cytotoxic to the EBV-negative Burkitt's lymphoma cell line DG-75

Figure 34:
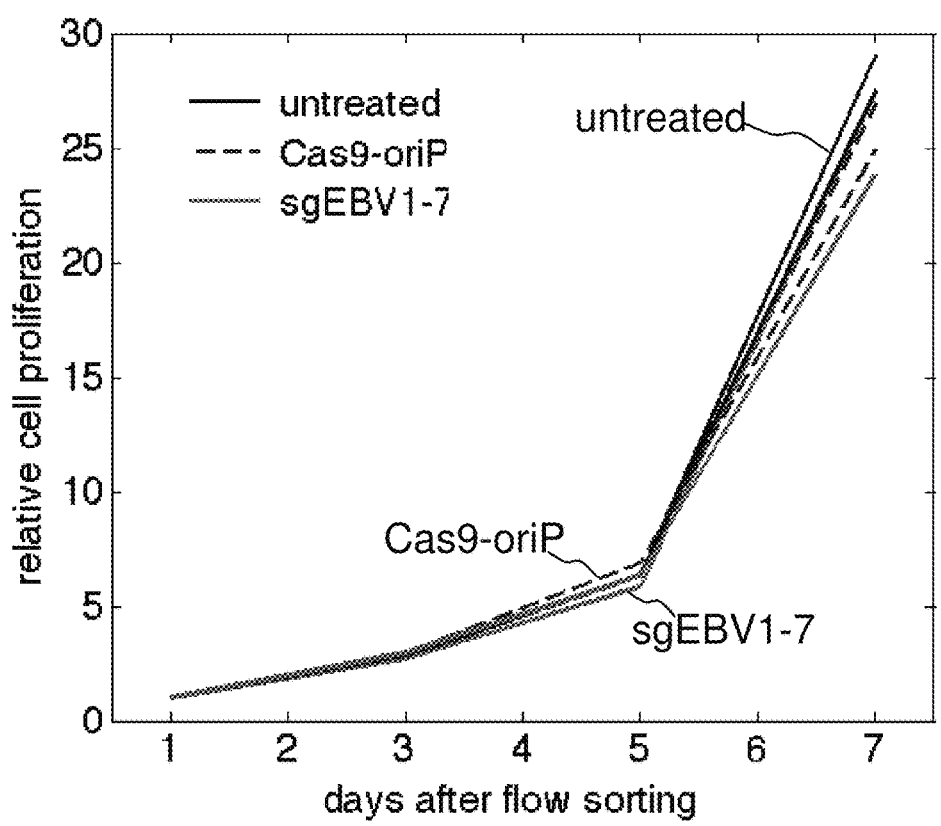
FIG. 34 shows that the CRISPR treatments were not cytotoxic to primary human lung fibroblasts IMR90.

FIG. 34 shows that the CRISPR treatments were not cytotoxic to primary human lung fibroblasts IMR90.

Eight and nine days after transfection the cell proliferation rates did not change from the untreated control groups, suggesting neglectable cytotoxicity.

Previous studies have attributed the EBV tumorigenic ability to its interruption of host cell apoptosis (Ruf IK et al. (1999) Epstein-Barr Virus Regulates c-MYC, Apoptosis, and Tumorigenicity in Burkitt Lymphoma. Molecular and Cellular Biology 19:1651-1660). Suppressing EBV activities may therefore restore the apoptosis process, which could explain the cell death observed in our experiment. Annexin V staining revealed a distinct subpopulation of cells with intact cell membrane but exposed phosphatidylserine, suggesting cell death through apoptosis (FIG. 18). Bright field microscopy showed obvious apoptotic cell morphology (FIG. 21) and fluorescent staining demonstrated drastic DNA fragmentation (FIG. 23). Altogether this evidence suggests restoration of the normal host cell apoptosis pathway after EBV genome destruction.

FIGS. 27-31 represent EBV load quantitation after CRISPR treatment.

Figure 27:
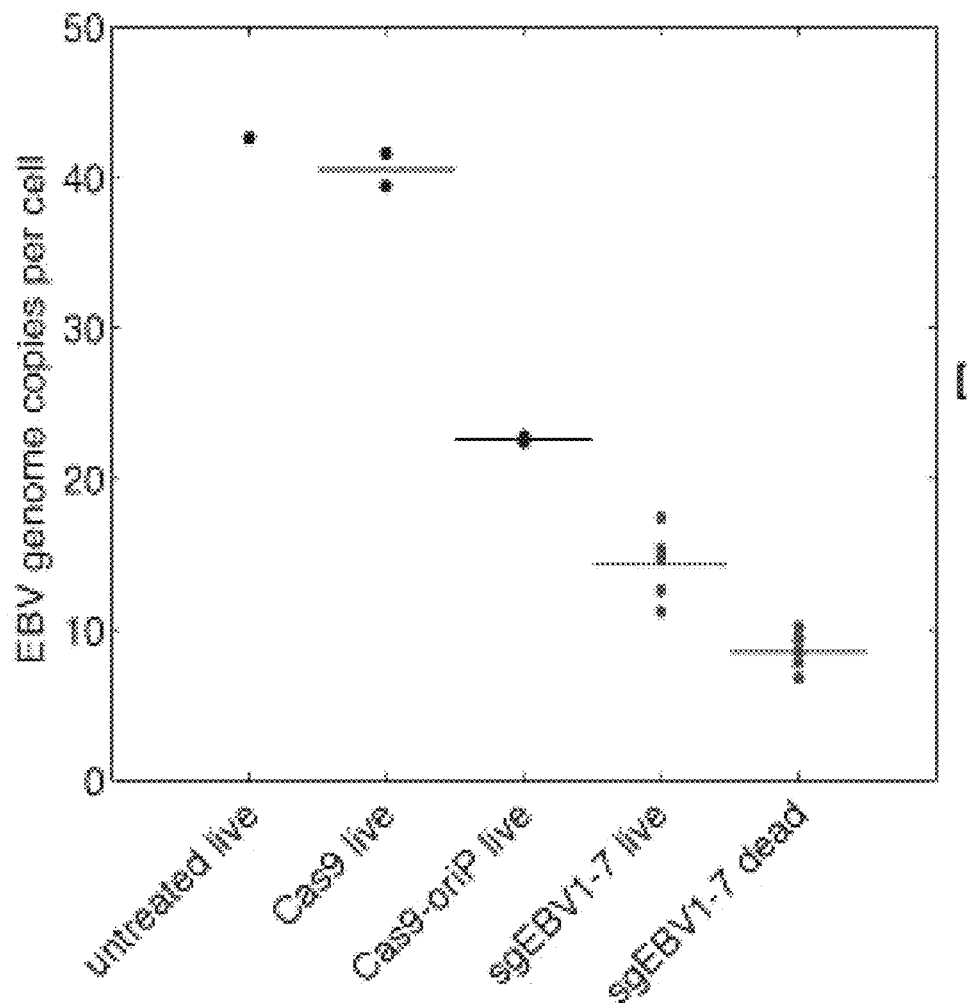
FIG. 27 shows EBV load after different CRISPR treatments by digital PCR. Cas9 and Cas9-oriP had two replicates, and sgEBV1-7 had 5 replicates.

FIG. 27 shows EBV load after different CRISPR treatments by digital PCR. Cas9 and Cas9-oriP had two replicates, and sgEBV1-7 had 5 replicates.

Complete Clearance Of EBV In A Subpopulation.

To study the potential connection between cell proliferation arrest and EBV genome editing, the EBV load was quantified in different samples with digital PCR targeting EBNA1. Another Taqman assay targeting a conserved human somatic locus served as the internal control for human DNA normalization. On average, each untreated Raji cell has 42 copies of EBV genome (FIG. 27). Cells treated with a Cas9 plasmid that lacked oriP or sgEBV did not have an obvious difference in EBV load difference from the untreated control. Cells treated with a Cas9-plasmid with oriP but no sgEBV had an EBV load that was reduced by ~50%. In conjunction with the prior observation that cells from this experiment did not show any difference in proliferation rate, we interpret this as likely due to competition for EBNA1 binding during plasmid replication. The addition of the guide RNA cocktail sgEBV1-7 to the transfection dramatically reduced the EBV load. Both the live and dead cells have >60% EBV decrease comparing to the untreated control.

Although seven guide RNAs were provided at the same molar ratio, the plasmid transfection and replication process is likely quite stochastic. Some cells will inevitably receive different subsets or mixtures of the guide RNA cocktail, which might affect the treatment efficiency. To control for such effects, the EBV load was measured at the single cell level by employing single-cell whole-genome amplification with an automated microfluidic system.

Freshly cultured Raji cells were loaded onto the microfluidic chip and captured 81 single cells.

For the sgEBV1-7 treated cells, the live cells were flow sorted eight days after transfection and captured 91 single cells.

Figure 28:
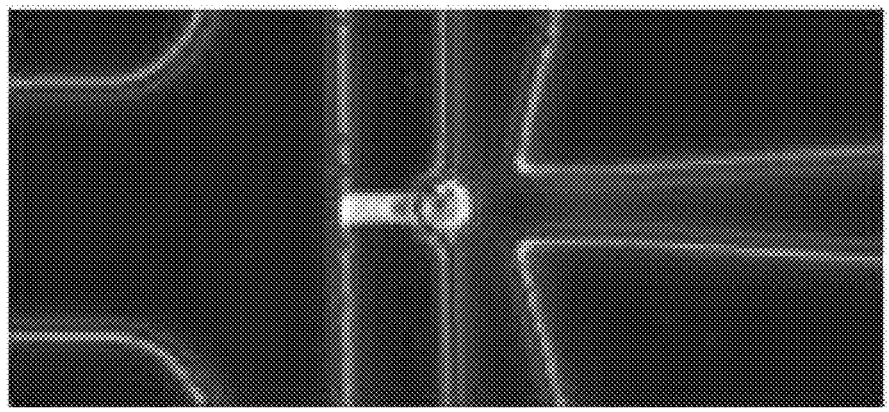
FIGS. 28 shows a single Raji cell as captured on a microfluidic chip.

FIGS. 28 shows a single Raji cell as captured on a microfluidic chip.

Figure 29:
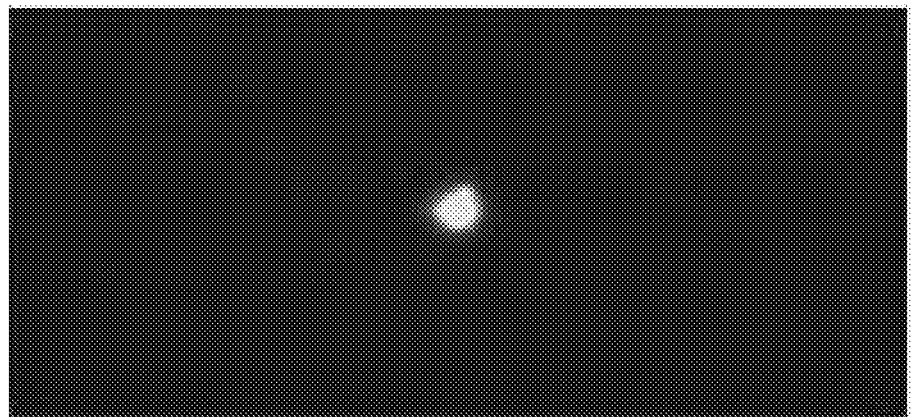
FIG. 29 shows a single sgEBV1-7 treated cell as captured on the chip.

FIG. 29 shows a single sgEBV1-7 treated cell as captured on the chip.

Following manufacturer's instruction, ~150 ng amplified DNA was obtained from each single cell reaction chamber. For quality control purposes we performed 4-loci human somatic DNA quantitative PCR on each single cell amplification product (Wang J, Fan H C, Behr B, Quake S R (2012) Genome-wide single-cell analysis of recombination activity and de novo mutation rates in human sperm. Cell 150:402-412) and required positive amplification from at least one locus.

Figure 30:
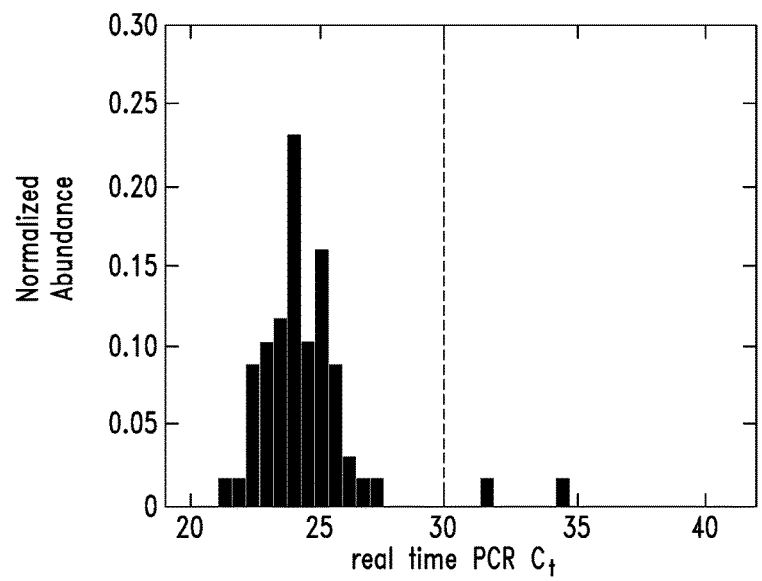
FIG. 30 is a histogram of EBV quantitative PCR Ct values from single cells before treatment.

FIG. 30 is a histogram of EBV quantitative PCR Ct values from single cells before treatment. The dash line represents Ct values of one EBV genome per cell. A log-normal distribution of EBV load was displayed by the 69 untreated single-cell products that passed the quality control, with almost every cell displaying significant amounts of EBV genomic DNA.

We calibrated the quantitative PCR assay with a subclone of Namalwa Burkitt's lymphoma cells, which contain a single integrated EBV genome. The single-copy EBV measurements gave a Ct of 29.8, which enabled us to determine that the mean Ct of the 69 Raji single cell samples corresponded to 42 EBV copies per cells, in concordance with the bulk digital PCR measurement. For the sgEBV1-7 treated sample, 71 single-cell products passed the quality control and the EBV load distribution was dramatically wider.

Figure 31:
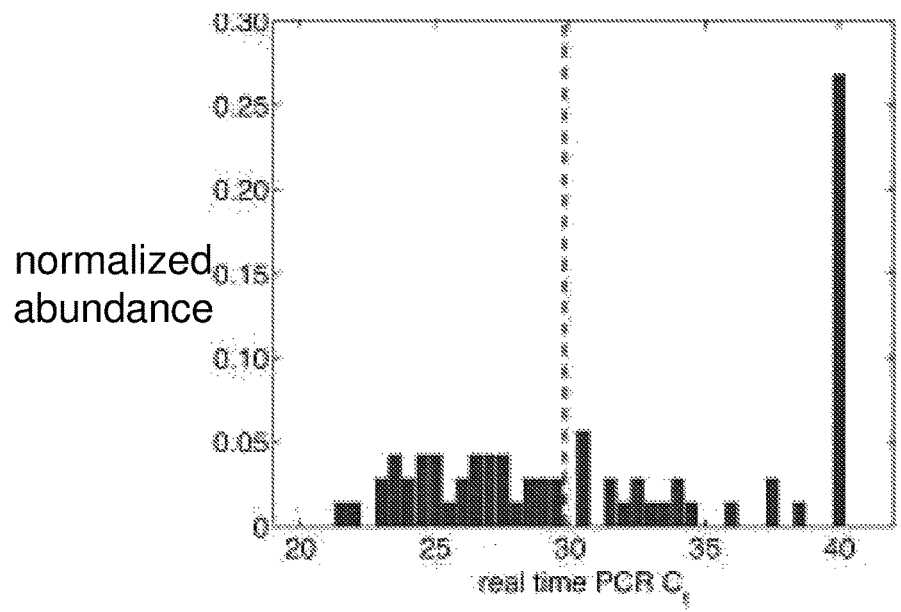
FIG. 31 is a histogram of EBV quantitative PCR Ct values from single live cells 7 days after sgEBV1-7 treatment.

FIG. 31 is a histogram of EBV quantitative PCR Ct values from single live cells 7 days after sgEBV1-7 treatment. The dash line represents Ct values of one EBV genome per cell.

While 22 cells had the same EBV load as the untreated cells, 19 cells had no detectable EBV and the remaining 30 cells displayed dramatic EBV load decrease from the untreated sample.

FIG. 32 represents SURVEYOR assay of EBV CRISPR. Lane 1 (lanes numbered from left to right): NEB 100 bp ladder; Lane 2: sgEBV1 control; Lane 3: sgEBV1; Lane 4: sgEBV5 control; Lane 5: sgEBV5; Lane 6: sgEBV7 control; Lane 7: sgEBV7; Lane 8: sgEBV4. FIG. 33 represents CRISPR cytotoxicity test with EBV-negative Burkitt's lymphoma DG-75. FIG. 34 represents CRISPR cytotoxicity test with primary human lung fibroblast IMR-90.

Essential Targets For EBV Treatment. The seven guide RNAs in our CRISPR cocktail target three different categories of sequences which are important for EBV genome structure, host cell transformation, and infection latency, respectively. To understand the most essential targets for effective EBV treatment, we transfected Raji cells with subsets of guide RNAs. Although sgEBV4/5 reduced the EBV genome by 85%, they could not suppress cell proliferation as effectively as the full cocktail (FIG. 14). Guide RNAs targeting the structural sequences (sgEBV1/2/6) could stop cell proliferation completely, despite not eliminating the full EBV load (26% decrease). Given the high efficiency of genome editing and the proliferation arrest (FIG. 2), we suspect that the residual EBV genome signature in sgEBV1/2/6 was not due to intact genomes but to free-floating DNA that has been digested out of the EBV genome, i.e. as a false positive. We conclude that systematic destruction of EBV genome structure appears to be more effective than targeting specific key proteins for EBV treatment.

What is claimed is:

1. A composition for treatment of a herpes simplex virus (HSV) infection, the composition comprising a vector encoding:

a Cas9 endonuclease; and a guide RNA having a portion complementary to an origin of replication S (oriS) region of HSV nucleic acid, the guide RNA capable of directing the Cas9 endonuclease to the region of HSV nucleic acid.

2. The composition of claim 1, wherein the composition is configured to be administered transdermally.

3. The composition of claim 1, wherein the composition comprises a topical solution.

4. The composition of claim 1, wherein the composition is packaged for delivery to a human patient.

5. The composition of claim 1, wherein the portion of the guide RNA complementary to the origin of replication S (oriS) region of HSV nucleic acid has no match >60% within a human genome.

6. The composition of claim 1, wherein the vector comprises one selected from the group consisting of: retrovirus, lentivirus, adenovirus, herpesvirus, poxvirus, alphavirus, vaccinia virus, adeno-associated viruses, a plasmid, a nanoparticle, a cationic lipid, a cationic polymer, metallic nanoparticle, a nanorod, a liposome, microbubbles, a cell-penetrating peptide, and a liposphere.

7. A method for treating a herpes simplex virus (HSV) infection, the method comprising:

introducing into a cell of a host,
(i) a vector encoding a Cas9 endonuclease and a guide RNA having a portion complementary to an origin of replication S (oriS) region of HSV nucleic acid, or
(ii) a ribonucleoprotein that includes the Cas9 endonuclease and a guide RNA having a portion complementary to an origin of replication S (oriS) region of HSV nucleic acid, wherein the guide RNA is capable of directing the Cas9 endonuclease to the region of HSV nucleic acid.

8. The method of claim 7, further comprising transdermally administering the vector or ribonucleoprotein to the host.

9. The method of claim 8, wherein the transdermal administration comprises applying a topical solution comprising the vector or ribonucleoprotein.

10. The method of claim 7, wherein the host is a living human subject and the method is performed in vivo.

11. The method of claim 7, wherein the portion of the guide RNA complementary to the origin of replication S (oriS) region of HSV nucleic acid has no match >60% within a human genome.

12. The method of claim 7, wherein the vector comprises one selected from the group consisting of: retrovirus, lentivirus, adenovirus, herpesvirus, poxvirus, alphavirus, vaccinia virus, adeno-associated viruses, a plasmid, a nanoparticle, a cationic lipid, a cationic polymer, metallic nanoparticle, a nanorod, a liposome, microbubbles, a cell-penetrating peptide, and a liposphere.

13. A composition for treatment of a herpes simplex virus (HSV) infection, the composition comprising a ribonucleoprotein, wherein the ribonucleoprotein comprises:

a Cas9 endonuclease; and
a guide RNA having a portion complementary to an origin of replication S (oriS) region of HSV nucleic acid, the guide RNA capable of directing the Cas9 endonuclease to the region of HSV nucleic acid.

14. The composition of claim 13, wherein the composition is configured to be administered transdermally.

15. The composition of claim 13, further comprising a pharmaceutically acceptable carrier for topical application to infected tissue.

16. The composition of claim 13, wherein the portion of the guide RNA complementary to the origin of replication S (oriS) region of HSV nucleic acid has no match >60% within a human genome.

17. A composition for treatment of a herpes simplex virus (HSV) infection, the composition comprising:

an mRNA encoding a Cas9 endonuclease; and
a guide RNA having a portion complementary to an origin of replication S (oriS) region of HSV nucleic acid, the guide RNA capable of directing the Cas9endonuclease to the region of HSV nucleic acid.

18. The composition of claim 17, wherein the mRNA and the guide RNA are encapsulated in or complexed with a lipid nanoparticle.

19. The composition of claim 17, wherein the composition comprises a topical solution.

20. The composition of claim 17, wherein the portion of the guide RNA complementary to the origin of replication S (oriS) region of HSV nucleic acid has no match >60% within a human genome.

21. The composition of claim 17, wherein the mRNA and the guide RNA are encapsulated in or complexed with a lipid nanoparticle.

* * * * *